United States Patent
Snoeck et al.

(10) Patent No.: US 9,988,606 B2
(45) Date of Patent: Jun. 5, 2018

(54) GENERATION OF AIRWAY AND LUNG PROGENITORS AND EPITHELIAL CELLS AND THREE-DIMENSIONAL ANTERIOR FOREGUT SPHERES

(71) Applicant: THE TRUSTEES OF COLUMBIA UNIVERSITY IN THE CITY OF NEW YORK, New York, NY (US)

(72) Inventors: Hans-Willem Snoeck, Brooklyn, NY (US); Sarah Xuelian Huang, New York, NY (US); Ya-Wen Chen, New York, NY (US); Jahar Bhattacharya, New York, NY (US); Mohammad Naeem Islam, Jamaica, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 296 days.

(21) Appl. No.: 14/417,273

(22) PCT Filed: Jul. 24, 2013

(86) PCT No.: PCT/US2013/051913
§ 371 (c)(1),
(2) Date: Jan. 26, 2015

(87) PCT Pub. No.: WO2014/018691
PCT Pub. Date: Jan. 30, 2014

(65) Prior Publication Data
US 2015/0247124 A1    Sep. 3, 2015

Related U.S. Application Data

(60) Provisional application No. 61/675,069, filed on Jul. 24, 2012, provisional application No. 61/834,404, filed on Jun. 12, 2013, provisional application No. 61/835,539, filed on Jun. 15, 2013.

(51) Int. Cl.
C12N 5/071 (2010.01)
G01N 33/68 (2006.01)
G01N 33/50 (2006.01)

(52) U.S. Cl.
CPC ......... *C12N 5/0689* (2013.01); *C12N 5/0688* (2013.01); *G01N 33/5044* (2013.01); *G01N 33/6887* (2013.01); *C12N 2501/11* (2013.01); *C12N 2501/115* (2013.01); *C12N 2501/117* (2013.01); *C12N 2501/119* (2013.01); *C12N 2501/15* (2013.01); *C12N 2501/155* (2013.01); *C12N 2501/16* (2013.01); *C12N 2501/385* (2013.01); *C12N 2501/40* (2013.01); *C12N 2501/415* (2013.01); *C12N 2506/02* (2013.01); *C12N 2506/23* (2013.01); *G01N 2333/78* (2013.01); *G01N 2500/04* (2013.01); *G01N 2500/10* (2013.01)

(58) Field of Classification Search
None
See application file for complete search history.

(56) References Cited

U.S. PATENT DOCUMENTS

| 4,514,420 A | 4/1985 | Imada et al. |
| 2012/0064050 A1 | 3/2012 | Calle et al. |
| 2014/0329318 A1* | 11/2014 | Rajagopal .......... G01N 33/6884 435/366 |

FOREIGN PATENT DOCUMENTS

| WO | 2011139628 | 11/2011 |
| WO | 2013106677 | 7/2013 |

OTHER PUBLICATIONS

Green et al., Generation of anterior foregut endoderm from human embryonic and induced pluripotent stem cells, Nature Biotechnology vol. 29 No. 3 Mar. 2011, published online Feb. 27, 2011; doi:10.1038/nbt.1788.*
Bennett et al., Regulation of Wnt Signaling during Adipogenesis, The Journal of Biological Chemistry, vol. 277, No. 34, Issue of Aug. 23, pp. 30998-31004, 2002.*
Longmire et al., "Efficient Derivation of Purified Lung and Thyroid Progenitors from Embryonic Stem Cells", Apr. 6, 2012, pp. 398-411, vol. 10, No. 4, Publisher: Cell Stem Cell, Published in: http://www.ncbi.nlm.nih.gov/pubmed/22482505.
Tompkins et al., "Sox2 is Required for Maintenance and Differentiation of Bronchiolar Clara, Ciliated, and Goblet Cells", Dec. 14, 2009, pp. 1-12, vol. 4, No. 12, Publisher: PLos One, Published in: http://www.ncbi.nlm.nih.gov/pubmed/20011520.
Yu et al., "Formation of Cysts by Alveolar Type II Cells in Three-Dimensional Culture Reveals a Novel Mechanism for Epithelial Morphogenesis", May 2007, pp. 1693-1700, vol. 18, Publisher: Molecular Biology of The Cell, Published in: http://www.ncbi.nlm.nih.gov/pubmed/17332496.
Seo et al., "Distinct Functions of Sox2 Control Self-Renewal and Differentiation of Osteoblast Lineage", Nov. 2011, pp. 4593-4608, vol. 31, No. 22, Publisher: Molecular Cell Biology, Published in: http://www.ncbi.nlm.nih.gov/pubmed/21930787.
Kim et al., "Alveolar Epithelial Cell Mesenchymal Transition Develops in Vivo During Pulmonary Fibrosis and is Regulated by the Extracellular Matrix", Aug. 29, 2006, pp. 13180-13185, vol. 103, No. 35, Publisher: Pnas, Published in: http://www.ncbi.nlm.nih.gov/pubmed/16924102.
ISA/US, "International Search Report and Written Opinion for the correspponding PCT/application US2013/51913", dated Nov. 29, 2013, pp. 1-4.

* cited by examiner

*Primary Examiner* — Taeyoon Kim
*Assistant Examiner* — Srikanth Patury
(74) *Attorney, Agent, or Firm* — Leason Ellis LLP

(57) ABSTRACT

Embodiments of the present invention are directed to various methods for generating airway and lung progenitors and epithelial cells and three-dimensional anterior foregut spheres, and to populations of cells made using the methods. The airway and lung progenitors and epithelial cells can be used as a model to study diseases that primarily affect airway epithelial cells, and to study human lung development. Methods are also provided for drug screening. Anterior foregut spheres can be used as a model for lung fibrosis.

15 Claims, 19 Drawing Sheets anteriorization: FGF2+SHH (Wong et al.)
lung field induction: FGF10+FGF7+BMP4 (5 ng/ml) (Wong et al)

anteriorization: DSM/SB>SB/I (Huang et al.)
lung field induction: FGF10+FGF7+BMP4 (5 ng/ml) (Wong et al)

anteriorization: FGF2+SHH (Wong et al.)
lung field induction: FGF10+FGF7+CHIR+BMP4 (50ng/ml)+RA (50nM)
(Huang et al)

GENERATION OF AIRWAY AND LUNG PROGENITORS AND EPITHELIAL CELLS AND THREE-DIMENSIONAL ANTERIOR FOREGUT SPHERES

CROSS-REFERENCE TO RELATED APPLICATIONS

This application is a 371 national stage application of PCT Application No. PCT/US2013/051913, filed Jul. 24, 2013, and claims the benefit of U.S. Provisional Application No. 61/835,539, filed on Jun 15, 2013, U.S. Provisional Application No. 61/834,404, filed on Jun. 12, 2013, and U.S. Provisional Application No. 61/675,069, filed on Jul. 24, 2012; the entire contents of which are hereby incorporated by reference as if fully set forth herein.

STATEMENT OF GOVERNMENTAL INTEREST

This invention was not made with government support.

BACKGROUND OF THE INVENTION

Lung disease kills 120,000 people in the U.S. every year. The lung is a highly complex organ however, containing dozens of different cell types, and regenerative medicine for lung disease is in its infancy. Novel approaches for cell replacement therapy for lung disease are therefore required. A first step in this field is the development of strategies to generate a variety of cell types of the lung from stem cells, and to understand the underlying mechanisms.

The ability to generate lung and airway epithelial cells has applications in regenerative medicine for lung diseases, drug screening and disease modeling, and provides a model to study human lung development. These include the recellularization of decellularized lung scaffolds to provide an autologous graft for transplantation, the study of human lung development, modeling of diseases that primarily affect airway epithelial cells, and drug screening[1].

BRIEF DESCRIPTION OF THE DRAWINGS

The present invention is illustrated by way of example, and not by way of limitation, in the figures.

SUMMARY OF THE INVENTION

Figure 1A:
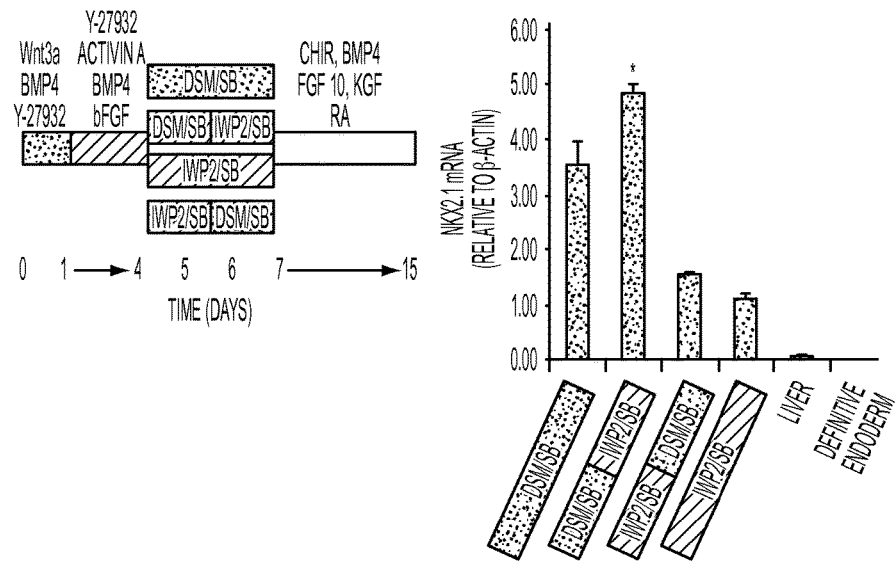
FIG. 1.(a) Expression of NKX2.1 mRNA at d15 in the four culture conditions shown at the left of the panel. *P<0.01, compared with IWP2/SB->DSM/SB group, triplicate experiments. 'Liver' represents DE cultured in the presence of BMP4 and bFGF, which specifies hepatic fate[13], data for definitive endoderm are samples analyzed at d4.5 of the differentiation protocol shown at the left of panel (a). (b) Effect of duration of endoderm induction on expression of NKX2.1 mRNA (left) and of NKX2.1 and FOXA2 protein (right) at d15 of the differentiation protocol shown on the upper left of the panel. The flow cytometric plots show the expression of the endoderm markers CXCR4 and c-KIT at the indicated time of dissociation of embryoid bodies. *P<0.01, compared with d4.5 or d5 dissociations, triplicate experiments representative of 3 independent experiments. 'Liver' represents DE cultured in 'hepatic conditions'[13].

Certain embodiments of the invention are directed to a method comprising culturing the AFE cells in a Wnt signaling agonist, RA and an agent that activates BMP4 signaling or BMP4 for at least 9 days, thereby producing lung and airway progenitor cells. The RA concentration can range from about 10 nM to about 1000 nM, but may vary based on the cell lines used. The Wnt signaling agonist includes GSK inhibitor including CHIR), a recombinant canonical Wnt agonists including Wnt3a, Norrin and R-Spondin, C19H18N4O3, and (2-amino-4-[3,4(methylenedioxy)benzylamino]6-(3-methoxyphenyl)pyrimidine. In an embodiment the AFE cells for use in the method above are made by (a) culturing mammalian definitive endoderm cells in a TGF-beta inhibitor and a BMP inhibitor for at least 1 day, and (b) culturing the cells of step (a) in a Wnt signaling inhibitor and a TGF-beta inhibitor for at least one day. In step a), the inhibitor of BMP can be Noggin, Chordin, Dorsomorphin(DSM), LDN 193189-DM 3189; Sclerostin, CTGF, gremlin or follistatin, and said inhibitor of TGF-beta signaling is SB-431542, and the TGF-beta inhibitor can be LY 364947, SB 431542, A 83-01, SD 208, GW 788388, SB 505124, SB 525334, RepSox, Casein Kinase I Inhibitor, D4476, AEBSF hydrochloride, and LY 2157299 (Galunisertib). BMP inhibitors include Dorsomorphin(DSM), LDN 193189, DM 3189; Sclerostin, chordin, CTGF, follistatin, and gremlin. The Wnt signaling inhibitor of step (b) includes IWP2, Dickkopf Dkk), RNAi targeting b-catenin, LRP, disheveled, dominant negative disheveled, dominant negative T-cell-specific transcription factor (TCF), Axin, Wnt inhibitory factor 1 (WIF-1), secreted Frizzled-related proteins (SFRP), Cerberus, Frzb, Wise, Sclerostin (SOST), WIF, Wise, Cerberus, IGFBP, Shisa, Waif1, APCDD1, and Tiki1.

In some embodiments the AFE is provided by a subject in need of an autologous lung or airway progenitor cell transplant, or an autologous lung or airway epithelial cell transplant or from a subject having a lung or airway disease.

In another embodiment for making airway and lung epithelial cells, clumps of the progenitor cells made as described above are selected, and then cultured in a Wnt signaling agonist and FGF agonist for a duration of time until airway and lung epithelial cells are detected. In an embodiment, KGF is added to the culture medium. The FGF can be FGF10 or FGF7, or both. Airway and lung epithelial cells made using this method include goblet cells, Clara cells, ciliated cells, type I alveolar cells, basal cells and type II alveolar epithelial cells. DCI is added in an embodiment to increase the production and maturation of alveolar type II cells. In an embodiment fluorescent surfactant beta to the cultures, and alveolar type II cells that express the fluorescent SB are isolated using flow cytometry.

Certain embodiments are directed to populations of cells made using the methods described herein, including an isolated population enriched for airway and lung progenitor cells, and an isolated population of cells enriched for airway and lung epithelial cells, comprising up to about 90% airway and lung epithelial cells, and an isolated population of lung epithelial cells enriched in alveolar type II.

In an embodiment hollow spheres of cells are made from lung progenitor cells by (a) collecting both adherent and non-adherent clusters of cells of lung progenitor cells made as described above, and (b) culturing the clusters in non-adherent culture conditions in the presence of a Wnt signaling agonist, RA and an agent that increases BMP4 signaling, including BMP4 until the clusters form hollow spheres, typically for about 15 days. In an embodiment the Wnt agonist is CHIR. This method optional comprises adding FGF10 and KGF to improve the longevity of cells in culture. Culturing the hollow spheres for an additional about 15 days results in the spheres forming ingrowths of cells; and culturing these spheres with ingrowths for about an additional 15 days results in the spheres collapsing. In some embodiments the cells in the spheres produce collagen. Some embodiments are directed to collagen-producing spheres. The cells in the spheres express lung markers. Inn certain embodiments the spheres contain lung and airway epithelial cells comprising goblet, Clara, ciliated, type I, type II alveolar epithelial cells or combinations thereof.

Some cells in the spheres express airway stem cell marker P63. In all of the embodiments the mammalian cells are preferably human cells.

Another embodiment is directed to a cell model for lung fibrosis, using isolated populations of cells enriched in lung and airway progenitor and epithelial cells and spheres made as described.

Other embodiments are directed to a test agent screening method having the steps of: providing a control and a test population spheres made by the method of claim 21, contacting the test population with a test agent, determining if the test agent prevents collagen formation in the test population compared to the control population; and if the test agent prevents collagen formation in the test population compared to the control population then identifying and selecting the test agent as one that may be useful in treating or preventing lung fibrosis. This method can further include the steps of (e) if the test agent does not prevent collagen formation, then continuing to culture the spheres in the presence of the test agent, (f) determining if the test agent prevents the spheres from forming ingrowths of cells, and (g) if the test agent prevents the ingrowth of cells into the spheres, then identifying and selecting the test agent as one that may be useful in treating or preventing lung fibrosis. The method can further include (h) if the test agent does not prevent the ingrowth of cells into the spheres, then continuing to culture the spheres with ingrowths in the test population in the presence of the test agent, and (i) if the test agent prevents the collapse of the spheres in the test population compared to the control population, then identifying and selecting the test agent as one that may be useful in treating or preventing lung fibrosis.

Some embodiments are directed to a biological scaffold comprising the lung and airway progenitor cells of claim 1, or the lung and airway epithelial cells, or populations enriched in type II alveolar cells.

Another embodiment is directed to a screening method to identify an agent that increases surfactant production in lung progenitor or lung epithelial cells having the steps of providing a control and a test population of progenitor cells, epithelial cells, or alveolar type II cells; contacting the test population with a test agent; determining if the test agent increases surfactant production in the test population compared to the control population; and if the test agent significantly increases surfactant production in the test population compared to the control population then identifying and selecting the test agent.

DETAILED DESCRIPTION

Embodiments of the present invention is directed to various methods for generating airway and lung progenitors and epithelial cells and three-dimensional anterior foregut spheres, and to populations of cells made using embodiments of the methods. The spheres can be used as a model for lung fibrosis, and for testing agents that are capable of reducing or blocking collagen production by the spheres.
Overview Embryonic stem (ES) cells are derived from the inner cell mass of the blastocyst and can be maintained in a pluripotent state in defined conditions. Without being bound by theory, they can be differentiated into every somatic and germ cell type. The development of appropriate conditions to differentiate ES into a variety of cell types and tissues therefore holds major promise for future cell replacement therapy. Furthermore, the recent discovery that adult somatic cells can be reprogrammed using a relatively simple procedure into a pluripotent state (induced pluripotent cells, or iPS cells) opens the way for the generation of patient-specific pluripotent cells, which would overcome rejection problems and ethical issues associated with the use of hES cell-derived tissues.

Lung development from endoderm is driven primarily by the combinatorial, spatially and temporally tightly regulated activation and inhibition of six signaling pathways: BMP/TGF FGF, Wnt, retinoic acid (RA), Hedgehog (HH) and Notch. The lung develops from the ventral aspect of the Foxa2+Sox2+ anterior foregut endoderm, from a region marked by the expression of Nkx2.1.

Trachea and bronchi are lined by a pseudostratified epithelium that contains ciliated, mucus (goblet), secretory (Clara), neuroendocrine, basal, and rare chemosensory 'tuft' or 'brush' cells[2]. The alveoli are lined by alveolar epithelial type I (ATI) cells that are essential for gas exchange, and ATII cells that produce surfactant, critical for the maintenance of alveolar integrity[2]. The respiratory system is derived from lung buds on the anterior ventral aspect of the definitive endoderm (DE)[4]. Directed differentiation of PSCs into pulmonary tissue should therefore proceed by first differentiating into DE, followed by ventral anterior foregut endoderm (AFE) and then specification of lung and airway lineages.

As used herein, "anterior foregut endoderm" refers to endoderm that is anterior to the endoderm that gives rise to the liver. One of ordinary skill in the art will readily appreciate that "anterior foregut endoderm" thus includes, for example, pharyngeal endoderm and other, more highly differentiated populations of endodermal cells and that the various cell types encompassed by the term "anterior foregut endoderm" may exhibit different expression patterns of molecular markers. One of ordinary skill in the art will appreciate that "anterior foregut endoderm" gives rise to various tissues, e.g., tonsils, tympanic membrane, thyroid, parathyroid glands, thymus, trachea, esophagus, stomach, lung and larynx/pharynx. Embryonic tissues express characteristic sets of molecular markers. Inner cell mass cells express transcription regulators OCT3/4, NANOG, and SOX2. Definitive endoderm cells express transcription regulators FOXA2, SOX17 and FOXA3. Anterior foregut endoderm cells express transcription regulators FOXA2 and SOX2. Pharyngeal endoderm cells express transcription regulators TBXI and SOX2. Third pharyngeal pouch cells express transcription regulators PAX1/9, HOXA3 and SIX I. Thymic epithelial cells express the transcription regulator FOXNI. The lung field of the anterior foregut endoderm expresses NKX2.1 and GATA6. The detection of anterior foregut endoderm markers in tissue is not, in and of itself, sufficient to demonstrate the presence of anterior foregut endoderm derived from ES cells. ES cells are maintained in an undifferentiated state under specific culture conditions. Removal of these conditions results in the formation of embryoid bodies (EBs), which are spheres of cells undergoing spontaneous gastrulation, leading to the random generation of derivatives of all germ layers that undergo random differentiation. EBs undergoing random differentiation express markers for many embryonic tissues, including markers for anterior foregut endoderm. Proper classification of ES derived tissues as anterior foregut endoderm thus requires additional characterization of tissue beyond mere expression of markers for anterior foregut endoderm, such as that cell fates not associated with anterior foregut endoderm are suppressed or that definitive endodermal and posterior endodermal signals are depleted is required.

Generation of Definitive Endoderm

Definitive endoderm was defined as a population of squamous cells that expressed Sox17, CXCR4 and Trh, which formed without the prior formation of primitive endoderm and was unable to endocytose horseradish peroxidase from the medium Vassilieva S, et al. Source. A system to enrich for primitive streak-derivatives, definitive endoderm and mesoderm, from pluripotent cells in culture, Epub 2012 Jun. 11.

Methods for making definitive endoderm (DE) starting from stem cells are well known in the art and are described inter alia in Snoeck et al., PCT/US2011/033751. One way to make DE includes: (a) culturing pluripotent stem cells with Wnt3a, BMP4, and Y-27932 for at least 1 day (for example day 1); (b) culturing the cells for at least 3 days (for example days 2-4) in the presence of Y-27932(optional, Activin A, BMP4 and Bfgf to obtain DE.

Generation of definitive endoderm from human ES or iPS cells may be accomplished by adapting a protocol used to develop definitive endoderm from mouse ES cells. Kubo et al., Development 131:1651-1662 (2004); Gadue et al., Proc Natl Acad Sci USA 103:16806-20 16811 (2006); Gouon-Evans et al., Nat Biotechnol, 24:1402-1411 (2006). In one method, human ES cells were pulsed with a low concentration of BMP4 (e.g., about 0.5-10 ng/ml, e.g., 1 ng/ml), cultured in low concentrations of BMP4 and bFGF (e.g., about 5-20 ng/ml, e.g., about 10 ng/ml), and then cultured in a high concentration of ActivinA (50-500 ng/ml, e.g., 75-150 ng/ml, e.g., about 100 ng/ml) on non-tissue-treated plastic, resulting in the formation of embryoid bodies (EBs). The EBs consisted virtually uniformly of endoderm. Development of endoderm may be confirmed by expression of CXCR4 and c-KIT. Development of endoderm is accompanied by loss of the ES marker, SOX2, and sequential gain ofMIXL1, SOX17 and FOXA2, up to day 5. Snoeck et al., PCT/US2011/033751.

It was previously demonstrated that AFE can be generated with high conversion efficiency by exposing DE to dual TGF-β and bone morphogenetic protein "BMP" inhibition[5]. These cells could be partially specified towards a putative lung bud fate, suggested by expression of NKX2.1. However, purity was <40%, and expression of specific markers for lung and airway epithelial cells was not detected.

Recently, differentiation of hPSC-derived lung progenitors has been reported, though with low efficiency, and only a few percent of NKX2.1$^+$p63$^+$ putative airway progenitors were obtained, while expression of markers for mature airway epithelial cells was not achieved[6]. In the mouse, a NKX2.1:GFP reporter ES line was used to isolate NKX2.1$^+$ cells after differentiation into AFE using a strategy very similar to our previously published protocol[5]. These were committed to a lung and thyroid fate, and were amenable to further differentiation, although expression of markers of ATI and ATII cells remained sporadic[7]. Wong et al. showed differentiation of hPSCs into CFTR-expressing cells[8]. However, no other types of lung or airway epithelial cells were generated.

New strategies to achieve better enrichment of developmental lung progenitor cells, and their differentiation into functional respiratory epithelial cells have now been discovered.

Embodiments of the Present Invention

Certain embodiments of the new methods are provided for inducing the differentiation of definitive endoderm or AFE into FOXA2$^+$NKX2.1$^+$ lung and airway progenitors in culture, i.e. AFE committed to lung and airway fate. More than 90% of these cells were committed to a lung or airway epithelial fate. In most of the embodiments the starting material for the methods is mammalian, preferably human, De, however, one can start with pluripotent cells: hPSCs or iPSCs.

In an embodiment for making lung and airway progenitors, AFE cells (from any source) are cultured in a Wnt signaling agonist, RA and an agent that activates BMP4 signaling or BMP4 for at least 9 days, thereby producing lung and airway progenitor cells. In an embodiment the amount of RA ranges from about 10 nM to about 1000 nM. In other embodiments additional factors are optionally added including the "ventralization cocktail" described in the examples. In an embodiment, about 80% -90% of all of the cells expressed NKX.2.1 and FOXA2 which identifies them as lung and airway progenitors.

While AFE from any source can be used, in an embodiment the AFE cells are made by (a) culturing mammalian definitive endoderm cells in a TGF-beta inhibitor and a BMP inhibitor for at least 1 day, and then (b) culturing the cells of step (a) in a Wnt signaling inhibitor and a TGF-beta inhibitor for at least one day.

Other embodiments include methods for making lung and airway epithelial cells from the progenitor cells. For example, clumps of the lung progenitor cells, made as described above are selected and replated for culturing in a Wnt signaling agonist and FGF agonist for a duration of time until airway and lung epithelial cells are detected. In another embodiment KGF, or other such as sonic hedghog, DAPT, cyclopamine, or EGF or combinations thereof are also added to the Wnt signaling agonist and FGF agonist. For the cells used in the Examples RUES2, the time for culturing in a Wnt signaling agonist and FGF agonist was about 21 days, but it can vary depending on the source of the definitive endoderm. The simplest way to determine if the cells have been cultured long enough is to stain a few wells for the markers of mature lung and airway cells. Replating the progenitor cells is done because the cells are confluent and replating removes some contaminating neural cells.

The lung and airway epithelial cells thus derived comprise goblet cells, Clara cells, ciliated cells, type I alveolar cells, basal cells and type II alveolar epithelial cells or combinations thereof. In an embodiment DCI is added at least 6 days after replating to enrich the production and maturation of type II alveolar cells, but this is variable with different cell lines. DCI comprises dexamethasone, 8-bromo-cAMP-, and IBMX (isobutylmethylxanthine) (3,7-Dihydro-1-methyl-3-(2-methylpropyl)-1H-purine-2,6 dione). In another embodiment dexamethasone is added alone. Importantly, the type II alveolar epithelial cells were capable of surfactant protein-B uptake, providing evidence of lung cell specific function. An embodiment is directed to an isolated population enriched in alveolar type II cells.

In a specific embodiment lung and airway progenitor cells can be made from anterior foregut endoderm cells, by: (a) culturing pluripotent stem cells with Wnt3a, BMP4 and Y-27932 for at least 1 day (for example day 1); (b) culturing the cells for at least 3 days (for example days 2-4) in the presence of Y-27932 (which is optional), Activin A, BMP4 and; (c) culturing the cells for at least 1 day in DMS/SB (for example day 5); (d) culturing the cells in IWP2SB for at least one day (for example day 6); (e) culturing the cells in CHIR99021, BMP4, FGF10 KGF AND RA for at least 9 days (for example days 7-15) to obtain lung progenitor cells. Lung and airway epithelial cells can be made from the progenitors by (f) selecting the lung and airway progenitor cells. Lung and airway epithelia from progenitor cells by (g) replating the lung and airway progenitor cells of step (f), (h)

culturing the replated cells for at least about 45 days (for example from day 15-60) in CHIR99021, FGF10 and KGF to obtain airway and lung epithelial cells, and (i) selecting the airway and lung epithelial cells.

Other embodiments are directed to a method to isolate type II alveolar epithelial cells from the lung and airway epithelial cells, using flow cytometric cell sorting after uptake of fluorescent surfactant protein B.

In other embodiments airway and lung epithelial cells are generated from pluripotent cells, DE or AFE from patients with lung or airway diseases including diseases that affect AT II cells, such as surfactant and ABCA3-deficiencies. In other embodiments the lung and airway epithelial cells, particularly the alveolar II cells, are used for disease modeling (viral infection, surfactant defects), drug screening to identify agents including small molecules to enhance surfactant production in premature infants, and to correct genetic defects in surfactant production, modeling of human lung cancer, regenerative medicine for human lung disease. The latter is critical as AT II cells play an important role in alveolar regeneration, in addition to producing lung surfactant, which is critical for normal lung function.

Inhibiting or removing agonists to signaling pathways critical for early lung development in the mouse, retinoic acid, Wnt and BMP, modeled defects observed in corresponding genetic mouse knockouts, thus validating this approach. Morrisey, E. E. & Hogan, B. L. Preparing for the first breath: genetic and cellular mechanisms in lung development. *Dev Cell* 18, 8-23 (2010); Goss, A. M. et al. Wnt2/2b and beta-catenin signaling are necessary and sufficient to specify lung progenitors in the foregut. *Dev Cell* 17, 290-298 (2009); Bellusci, S., et al., Evidence from normal expression and targeted misexpression that bone morphogenetic protein (Bmp-4) plays a role in mouse embryonic lung morphogenesis. *Development* 122, 1693-1702 (1996); Domyan, E. T. et al. Signaling through BMP receptors promotes respiratory identity in the foregut via repression of Sox2. *Development* 138, 971-981 (2011); Li, Y., et al. Bmp4 is required for tracheal formation: a novel mouse model for tracheal agenesis. *Developmental biology* 322, 145-155 (2008); and Chen, F. et al. A retinoic acid-dependent network in the foregut controls formation of the mouse lung primordium. *J Clin Invest* 120, 2040-2048 (2010).

The new methods provide a robust in vitro model where cell numbers are not limiting that behaves in a fashion consistent with mouse lung development in vivo and differentiation of NKX2.1$^+$FOXA2$^+$ cells into cells expressing markers of lung and airway epithelial lineages. Until the work described here, there was no adequate in vivo assay to test the function of lung and airway epithelial cells, as engraftment of cells in lung injury models has never been convincingly demonstrated. This is important for understanding of lung development in humans, for disease modeling and drug screening. Importantly, the methods permit the generation of autologous lung and airway epithelial cells for implantation and for seeding decellularized lung matrices, which include generating sufficient numbers of cells with the appropriate variety and ratio of epithelial cells normally found in the lung.

Another embodiment is directed to an isolated cell population enriched for airway and lung epithelial cells, especially type II alveolar cells, made by the methods above, wherein in an embodiment up to about 95% of the cells express NKX2.1, FOXA2, SOX2 or a combination thereof, or wherein up to about 86% of the cells are lung and airway epithelial specific cells.

Generation of Spheres of Cells Grown from Human Pluripotent Stem Cells and DE Committed to an Anterior Foregut Lineage Pulmonary fibrosis is the formation or development of excess fibrous connective tissue (fibrosis) in the lungs, also described as "scarring of the lung." Pulmonary fibrosis may be a secondary effect of other diseases. Most of these are classified as interstitial lung diseases. Examples include autoimmune disorders, viral infections or other microscopic injuries to the lung. However, pulmonary fibrosis can also appear without any known cause (termed "idiopathic").

Pulmonary fibrosis involves gradual exchange of normal lung parenchyma with fibrotic tissue. The replacement of normal lung with scar tissue causes irreversible decrease in oxygen diffusion capacity. In addition, decreased compliance makes pulmonary fibrosis a restrictive lung disease. It is the main cause of restrictive lung disease that is intrinsic to the lung parenchyma. Diseases and conditions that may cause pulmonary fibrosis as a secondary effect include: Inhalation of environmental and occupational pollutants, such as in asbestosis, silicosis and exposure to certain gases; and hypersensitivity pneumonitis, most often resulting from inhaling dust contaminated with bacterial, fungal, or animal products. Some typical connective tissue diseases include rheumatoid arthritis, SLE and scleroderma. Other diseases that involve connective tissue include sarcoidosis and Wegener's granulomatosis, and infections. Fibrosis can also be caused by certain medications, e.g. amiodarone, bleomycin (pingyangmycin), busulfan, methotrexate, and nitrofurantoin and radiation therapy to the chest.

Treatment options for idiopathic pulmonary fibrosis are very limited. Though research trials are ongoing, there is no evidence that any medications can significantly help this condition. Lung transplantation is the only therapeutic option available in severe cases. Since some types of lung fibrosis can respond to corticosteroids (such as Prednisone) and/or other medications that suppress the body's immune system, these types of drugs are sometimes prescribed in an attempt to slow the processes that lead to fibrosis. New drugs for treating lung fibrosis are needed. Such drugs are typically best discovered using a model system that permits efficient drug screening.

Certain embodiments are directed to a new model system for interstitial lung fibrosis suitable for disease modeling, mechanistic studies and drug discovery. This model is based on culturing ventral anterior foregut endoderm (AFE) to generate spheres of cells grown from human pluripotent stem cells committed to an anterior foregut lineage. The cultured AFE cells form hollow spheres that eventually develop ingrowths of cells. The hollow spheres with the ingrowths of cells eventually express collagen in culture, and then collapse. It hypothesized that the collapse of the spheres is caused by ingrowth of cells that undergo epithelial-to-mesenchymal transition at which time they begin to produce connective tissue (reflected by the production of collagen) and thus cause the spheres to 'contract,' i.e. collapse. This forming of collagen is thought to reflect formation of connective tissue such as is seen in fibrosis. The collagen-producing spheres having ingrowths of cells are involved in regenerating mature (adult) lung cells at the late stage of culture. Collagen production can be detected using Masson's trichrome staining, however any method known in the art can be used, including visualization with anti-collagen antibodies, or PCR detection of collagen mRNA.

Ingrowths of cells into the hollow spheres are observed about 15 days after the hollow spheres appear. Some of the cells in the ingrowths express the airway stem cell marker P63 (FIG. 4, third upper panel). After about an additional 15 days, the spheres with the ingrowths of cells begin to 'collapse' (FIG. 2, lower right panel), and much more numerous cells are observed within the spheres (FIG. 5). The duration of time needed to form hollow spheres, ingrowths and collapsed spheres is typically about 15 days, but will vary depending on culture conditions and the cell lines. These ingrowing cells are negative for the endodermal markers FOXA2 and SOX2 and the lung marker NKX2.1 (FIG. 5) showing that these cells are not endodermal. They arise either from contaminating mesoderm, or through epithelial to mesenchymal transition from endodermal cells.

After about day 36 in culture, the first evidence of a small amount of collagen deposition is observed in spheres with ingrowths using Trichrome Masson staining (FIG. 6). More collagen was seen by day 45. It is possible, and even likely, that the collapse of the spheres that begins after about 40-45 days in culture is caused by ingrowth of cells that undergo epithelial-to-mesenchymal transition, begin to produce connective tissue (collagen) and thus cause the spheres to 'contract' or collapse.

The basic protocol for generating spheres of cells grown from DE committed to an anterior foregut fate in culture is described in the examples. Examples of forming DE from hESC or IPSC is described in the examples and in PCT/US11/33751, U.S. Ser. No. 13/643,032 and Provisional application Nos. 61/675,069, filed Jul. 24, 2012, U.S. Provisional Application No. 61/834,404, filed Jun. 12, 2013, and U.S. Provisional Application No. 61/835,539.

In other embodiments of the invention the various protocols described herein and in the claims can be used to test the ability of a test agent to block formation of hollow spheres, or block the ingrowth of cells into the spheres, block collagen formation, or block the collapse of the spheres having ingrowths of cells. Agents that can block these transitions, particularly those that block collagen formation or sphere collapse, warrant further testing as possible therapeutic agents for preventing lung fibrosis.

BMP, Wnt and TGF-beta Inhibitors and Wnt Agonists

Over the past 20 years the transforming growth factor-β (TGF-β) family of secretory polypeptides has emerged as a major source of signals exerting this type of control. This family includes inter alia various forms of TGF-β, and the bone morphogenetic proteins (BMPs).

Signal transduction through BMfPRs results in mobilization of members of the SMAD family of proteins. BMP4 and its inhibitors noggin and chordin and follistatin help regulate polarity of the embryo (i.e. back to front patterning). The deployment of a cell's genetic program in a multicellular organism must be tightly controlled for the sake of the organism as a whole. Another class of BMP inhibitors includes the proteins that bind to BMP receptors but have no inherent signaling function and thus act as BMP receptor antagonists. To date, inhibin and BMP-3 have been identified as BMP receptor antagonists that can block BMP signaling in bone. BMP inhibitors further include Dorsomorphin (DSM), LDN 193189 (synonymous with DM 3189); Sclerostin, CTGF, gremlin, GDF3 protein, and 4-[6-[4-(1-methylethoxy)phenyl]pyrazolo[1,5-a]pyrimidin-3-yl]quinoline (DMH1) (synonymous: BMP Inhibitor II, referenced under CAS 1206711-16-1).

Wnt signaling inhibitors include IWP2, Dickkopf (Dkk) RNAi targeting b-catenin or LRP or disheveled, dominant negative disheveled, dominant negative TCF, or Axin, Wnt inhibitory factor 1 (WIF-1), secreted Frizzled-related proteins (SFRP), Cerberus, Frzb, Wise, Sclerostin (SOST), WIF, Wise, Cerberus, IGFBP, Shisa, Waif1, APCDD1, and Tiki1. Wnt signaling agonists include GSK inhibitors including CHIR, recombinant canonical Wnt agonists including Wnt3a, non-Wnt proteins including Norrin and R-Spondin, C19H18N4O3, and 2-amino-4-[3,4-(methylenedioxy)benzylamino]-6-(3-methoxyphenyl)pyrimidine.

TBF-beta inhibitors include anti-TGF-beta antibodies and the compounds in the table below.

TABLE 1

TGF-β inhibitors

| Name of Compound | Catalog No. | Description |
|---|---|---|
| SB 431542 | 1614/1 | Potent, selective inhibitor of TGF-betaRI, ALK4 and ALK7 |
| A 83-01 | 1614/10 | Potent, selective inhibitor of TGF-betaRI, ALK4 and ALK7 |
| SD 208 | 3269/10 | Potent ATP-competitive TGF-betaRI inhibitor |
| LY 364947 | 2718/1 | Selective inhibitor of TGF-betaRI |
| GW 788388 | 3264/10 | Selective inhibitor of TGF-betaRI |
| SB 505124 | 3263/10 | Selective inhibitor of TGF-betaRI, ALK4 and ALK7 |
| SB 525334 | 3211/10 | Selective inhibitor of TGF-betaRI |
| RepSox | 3742/10 | Selective inhibitor of TGF-betaRI |
| Casein Kinase I Inhibitor, D4476 | sc-202522 | Casein Kinase I Inhibitor, D447 is a cell-permeable triaryl substituted imidazolo compound that acts as a selective inhibitor of casein kinase 1 (CK1) and TGF-β type-I receptor (ALK5). CAS # 301836-43-1 |
| AEBSF, Hydrochloride | sc-202041 | AEBSF, Hydrochloride is a broad spectrum, water soluble, irreversible serine protease inhibitor. Serves as a stable, nontoxic alternative to PMSF (sc-3597) and DFP. CAS # 30827-99-7 |
| LY 2157299 (Galunisertib) | | |

TABLE 2

BMPs

| BMP | |
|---|---|
| BMP1 | BMP1 does not belong to the TGF-β family of proteins. It is a metalloprotease that acts on procollagen I, II, and III. It is involved in cartilage development. |
| BMP2 | Acts as a disulfide-linked homodimer and induces bone and cartilage formation. It is a candidate as a retinoidmediator. Plays a key role in osteoblast differentiation. |
| BMP3 | Induces bone formation. |
| BMP4 | Regulates the formation of teeth, limbs and bone from mesoderm. It also plays a role in fracture repair, epidermis formation, dorsal-ventral axis formation, and ovarian follical development. |
| BMP5 | Performs functions in cartilage development. |
| BMP6 | Plays a role in joint integrity in adults. Controls iron homeostasis via regulation of hepcidin |
| BMP7 | Plays a key role in osteoblast differentiation. It also induces the production of SMAD1. Also key in renal development and repair. |
| BMP8a | Involved in bone and cartilage development. |
| BMP8b | Expressed in the hippocampus. |
| BMP10 | May play a role in the trabeculation of the embryonic heart. |
| BMP15 | May play a role in oocyte and follicular development. |

Drug Screening

The present invention provides a method for screening for a test agent that inter alia prevents the formation of collagen in spheres of lung and airway cells, as described herein. Another screening embodiment identifies test agents that increase surfactant production in a population of cells made by the present methods.

Examples of the agents include protein, peptide, nonpeptidic compound, synthesis compound, fermentation product, cell extract, plant extract, animal tissue extract and the like. a nucleic acid, a peptide, a protein, a nonpeptidic compound, a synthetic compound, a fermentation product, a cell extract, a cell culture supernatant, a plant extract, a mammalian tissue extract, a plasma, or the like. The test substance may be a novel substance or a known substance. The test substance may be in the form of a salt and such a salt may be a salt with a physiologically acceptable acid or base. These substances may be novel or known. In addition, compound library produced using a combinatorial chemistry technique, random peptide library produced by solid phase synthesis or phage display, and the like are also preferable examples of the test substances.

As used herein, the term "test agent" can refer to pharmaceutical or non-pharmaceutical compounds or substrates which are assessed for the ability to block collagen formation in spheres of lung and airway cells as described herein, or that prevent the collapse of collagen-expression spheres.

In one embodiment, cultured spheres or other test cells are treated with a small molecular weight test reagent that can transport through the cell membrane. The amount of such agent may be determined by one skill in the art, but may generally be between about 0.01 micromolar (0.01 µM) to 1 mM.

Any assay that detects collagen or surfactant production can be used to monitor the efficacy of the test agent. Collapse of spheres expressing collagen can be assessed visually.

The duration of contact of the cultured spheres or other test cells with the test compound can be varied. Determination of the ability of the compound to prevent collage formation or collapse of the spheres or to increase or decrease surfactant production may be done at any time as long as it is after the start of the administration of the test substance.

In an embodiment progenitor cells and/or the epithelial cells may be used to screen for agents that significantly increase ion transport in abnormal CF cells from a CF subject. CF is caused by a mutation in the gene for the protein cystic fibrosis transmembrane conductance regulator (CFTR). This protein is required to regulate the components of sweat, digestive fluids, and mucus. CFTR regulates the movement of chloride and sodium ions across epithelial membranes, such as the airway epithelia. In an embodiment, airway epithelial cells generated using the methods of the embodiments from a CF subject-derived iPS cells are cultured and contacted with a test agent under conditions and for a duration of time that permits the test agent to alter ion transport across the cell membrane. Test agents that significantly increase sodium and chloride ion transport are select and tested further as potential therapeutic agents. By significantly increase (or decrease) is meant an increase (or decrease) of at least about 10% compared to controls.

Libraries screened using the methods of the present invention can comprise a variety of types of compounds. In some embodiments, the compounds are peptide molecules. In a non-limiting example, peptide molecules can exist in a phage display library. In other embodiments, types of compounds include, but are not limited to, peptide analogs including peptides comprising non-naturally occurring amino acids, e.g., D-amino acids, phosphorous analogs of amino acids, such as .alpha.-amino phosphoric acids and α-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used.

In an embodiment, the combinatorial libraries are small organic molecule libraries, such as, but not limited to, benzodiazepines, isoprenoids, thiazolidinones, metathiazanones, pyrrolidines, morpholino compounds, and diazepindiones. In another embodiment, the combinatorial libraries comprise peptoids; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available (see, e.g., Advanced ChemTech Europe Ltd., Cambridgeshire, UK; ASINEX, Moscow Russia; BioFocus plc, Sittingbourne, UK; Bionet Research (A division of Key Organics Limited), Camelford, UK; ChemBridge Corporation, San Diego, Calif.; ChemDiv Inc, San Diego, Calif.; ChemRx Advanced Technologies, South San Francisco, Calif.; ComGenex Inc., Budapest, Hungary; Evotec OAI Ltd, Abingdon, UK; IF LAB Ltd., Kiev, Ukraine; Maybridge plc, Cornwall, UK; PharmaCore, Inc., North. Carolina; SIDDCO Inc, Tucson, Ariz.; TimTec Inc, Newark, Del.; Tripos Receptor Research Ltd, Bude, UK; Toslab, Ekaterinburg, Russia).

In one embodiment, the combinatorial compound library for the methods of the present invention may be synthesized.

Exemplary synthetic low molecular weight biologically active molecules contemplated for use herein include MaxiVerse™ from Molecular Diversity Libraries (MolBio), LOPAC.sup.1280 (from Sigma), MyriaScreen Diversity Collection of drug-like screening compounds (from Sigma), compound libraries available on the world-wide web from biofocus.com/offerings/compound-libraries.htm?gclid=CMXYzorejp4CFSZdagodh-ktmsw, and the like, as well as combinations of any two or more thereof.

Additional exemplary naturally occurring and synthetic low molecular weight biologically active molecules contemplated for use herein include antiproliferatives, enzyme inhibitors, cell cycle regulators, apoptosis inducers, GPCR ligands, second messenger modulators, nuclear receptor ligands, actin and tubulin modulators, kinase inhibitors, protease inhibitors, ion channel blockers, gene regulation agents, lipid biosynthesis inhibitors, phosphodiesterase inhibitors, G-Proteins, cyclic nucleotides, multi-drug resistance, neurotransmission inhibitors, phosphatase inhibitors, and the like.

Exemplary polypeptides contemplated for use herein include protein transduction domain (PTD) peptides, and the like, as well as combinations of any two or more thereof.

Exemplary biopolymers contemplated for use herein include polyalkylene oxides, poly(ethylene glycol-co-acryloyl glycolic caproic acid), poly(acryloyl-6-amino caproic acid), poly(acryloyl-2-acrylamido glycolic acid), poly(2-hydroxyethyl methacrylate), poly(N-isopropylacylamide), poly(trimethylene carbonate), poly(acryloyl-4-aminobenzoicacid), poly(acrylamido-methyl-propane sulfonate), poly(3-(methacryloylamino)propyl)dimethyl(3-sulfopropyl)ammonium hydroxide), poly(3-(methacryloylamino)propyl) timethylammonium chloride, poly(ethylene-co-acrylic acid), poly(acrylic acid), poly(L-lactide), poly(D-lactide), poly(DL-lactide-co-glycolide) 85:15, poly(DL-lactide-co-glycolide) 75:25, poly(DL-lactide-co-glycolide) 65:35, poly(DL-lactide-co-caprolactone) 86:14, poly(DL-lactide-cocaprolactone) 40:60, polycaprolactone, poly(3-hydroxybutyric acid-co-3-hydroxyvaleric acid), poly(3-hydroxybutyric acid), polypropylene carbonate), poly(methyl vinyl ether-alt-maleic anhydride), hydrophilic, poly(sodium 4-styrenesulfonate), poly-L-arginine hydrochloride, poly-D-lysine hydrobromide, poly-L-glutamic acid sodium salt, poly-L-ornithine hydrobromide, poly(2-ethyl-2-oxazoline), poly(oligoethylene glycol methyl ethyl methacrylate), poly(butyl methacrylate), poly(ethyl methacrylate), poly(styrene-co-methacrylic acid), poly-L-arginine hydrochloride, poly(ethylene glycol)methacrylate, poly(styrene-alt-maleic acid), poly(styrene), poly(ethylene-alt-maleic anhydride), poly(4-styrenesulfonic acid-co-maleic acid), poly(methyl vinyl ether-alt-maleic acid), poly(methyl vinyl ether), poly(styrene-co-maleic anhydride), poly(isobutylene-co-maleic acid), poly(maleic anhydride-alt-1-octadecene), poly(styrene-alt-maleic anhydride), partial methyl ester, poly(ter-butyl methacrylate), poly(2-hydroxyethyl methacrylate), poly(benzyl methacrylate), poly(2-(dimethylamino)ethyl methacrylate), poly(4-vinylphenol-co-methyl methacrylate), poly(ethylene-co-gylcidyl-methacrylate), poly(cyclohexyl methacrylate), poly(tert-butyl acrylate-co-ethyl acrylate-co-methacryalic acid), poly(ethylene-co-methyl acrylate-co-glycidyl methacrylate), poly(ethylene-co-acrylic acid), poly(ethylene-co-acrylic acid), poly(vinyl alcohol), poly(vinylphosphonic acid), poly(vinyl sulfate) potassium salt, poly(4-vinylpyridine hydrochloride), poly(4-vinylphenol), poly(4-vinylpyridine) crosslinked, poly(vinyl-co-ethylene), poly(vinyl butyral-co-vinyl alcohol-co-vinyl acetate), poly(ethylene-co-vinyl acetate-co-carbon monoxide), poly(allylamine hydrochloride), poly(anetholesulfonic acid), poly(epoxysuccinic acid), poly(1,4-butylene terephthalate), poly(styrene-co-4-bromostyrene-co-divinylbenzene), poly(1,6-hexanediol/neopentyl glycol-alt-adipic acid), poly(acrylonitrile), poly(styrene-co-allyl alcohol), poly(N',N'-(1,3-phenylene)-isophthalamide), poly(trimellitic anhydride chloride-co-4',4'-methylene-dianiline), poly(Bisphenol A carbonate), poly(azelaic anhydride), poly(trimethylolpropane di(propylene glycol)-alt-adipic acid/phthalic anhydride), poly(di(ethylene glycol adipate), poly(allyamine), poly(diallyl dimethyl ammonium), poly(diallyl methylamine hydrochloride), poly(1-glyceryl monomethacrylate), poly(3-chroloro-2-hydroxypropyl-2-methacroxyethydimethylammonium chloride), poly(butadienne maleic acid), poly(vinyl pyrroliodone), poly(n-vinylpyrrolidone-vinylacetate), poly(ethylenimine), chitosan, poly(1-glyceryl monomethacrylate), and the like, as well as combinations of any two or more thereof.

Exemplary antibodies contemplated for use herein include any antibody (or fragment thereof) that can functionally interact with human cell types, whether said antibody is monoclonal or polyclonal. Exemplary antibodies include antibodies of the immunoglobulin subtype, Fab fragments, and the like, e.g., antibodies: which recognize cell surface markers unique to the target cell population; which recognize any cell surface protein(s) the expression of which is induced by exposure to multi-factorial media; which inhibit known cell signaling pathways; or which activate known cell signaling pathways, and the like, as well as combinations of any two or more thereof.

Exemplary nucleic acids contemplated for use herein include oligonucleotides, DNA molecules, RNA molecules, and the like, as well as combinations of any two or more thereof.

Exemplary DNA molecules contemplated for use herein include DNA-plasmids/vectors encoding Zinc-finger nucleases, Zinc-finger transcription factors, cDNA over-expression libraries, and the like, as well as combinations of any two or more thereof.

Exemplary RNA molecules contemplated for use herein include siRNA (see, for example, sigmaaldrich.com/life-science/functional-genomics-and-mai/sima.html on the world-wide web), shRNA (see, for example, (sigmaaldrich.com/life-science/functional-genomics-and-mai.html and openbiosystems.com/RNAi/shrnaLibraries/ as available on the world-wide web), microRNA (see, for example, mirbase.org/index.shtml as available on the world-wide web), and the like, as well as combinations of any two or more thereof. As readily recognized by those of skill in the art, RNA molecules can be spotted onto an array either directly (e.g., using siRNA or microRNA), or as a virus containing a viral expression vector containing the RNA molecule of interest (e.g., microRNA or shRNA).

Exemplary lipids contemplated for use herein, or components thereof, include fatty acyls, glycerolipids, glycerophospholipids, sphingolipids, sterol lipids, prenol lipids, saccharolipids, polyketides, and the like, as well as combinations of any two or more thereof.

Exemplary vitamins and metabolites thereof (e.g., retinoic acid is a metabolite of Vitamin A), or functional components thereof, include vitamin A, vitamin B, vitamin C, vitamin D, vitamin E, vitamin K, and the like, as well as combinations of any two or more thereof.

Exemplary inorganic salts contemplated for use herein, or functional components thereof, include calcium chloride ($CaCl_2$), ferric nitrate ($Fe(NO_3)$), magnesium sulfate ($MgSO_4$), potassium chloride (KCl), sodium bicarbonate ($NaHCO_3$), sodium chloride (NaCl), sodium phosphate dibasic ($Na_2HPO_{0.4}$—$H_2O$), cupric sulfate, manganous chloride, sodium selenite, zinc sulfate ($ZnSO_4$-$7H_2O$), sodium phosphate monobasic ($NaH_2PO_4$—$H_2O$), Magnesium chloride (anhydrous), ferric sulfate ($FeSO_4$-$7H_2O$), and the like, as well as combinations of any two or more thereof.

The screening methods of the present invention for screening a library of test compounds preferably comprise contacting a test compound with a target cultured cells, preferably under physiologic conditions.

EXAMPLES

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1

Methods

Immunofluorescence Staining of Spheres

The clumps/spheres collected at different time points were preserved in O.C.T. The samples were sectioned (5-10 µm/section) using cryostat and were fixed with 4% paraformaldehyde for 20 minutes at room temperature (RT) and washed twice with DPBS. The slides were permeabilized in 0.25% Triton X-100/PBS for 20 minutes followed by blocked in 5% fetal donkey serum/PBS for 1 hour at RT. The slides were stained with a combination of two or three primary antibodies listed as below overnight at 4° C. FOXA2/HNF-3β (goat, Santa Cruz Biotechnology. Inc., Santa Cruz, Calif., Cat#sc-6554, clone M-20, 1:50), TTF-1/Nkx2.1 (mouse, Invitrogen, 18-0221, clone 8G7G3/1, 1:100), TTF-1/Nkx2.1 (Rabbit, Seven Hills Bioreagents, Cincinnati, Ohio, Cat#WRAB-1231, 1:1000), p63α (rabbit, Santa Cruz, sc-8344, clone H-129, 1:100), Sox2 (Rabbit, stemgent, 09-0024, 1:100), Pax 6 (rabbit, Covance, Princeton, N.J., Cat#PRB-278P, 1:300), Pax8 (mouse, Abcam, Cambridge. Mass, Cat#ab53490, 1:100), EpCAM (APC conjugated, mouse, BD Biosciences, BDB347200), Tuj1 (mouse, Sigma, T8578, Clone 2G10, 1:4000), Mucin5AC (mouse (Biotin), Abcam, ab79082, clone 45M1, 1:100), Mucin5B (rabbit, Santa Cruz, sc-20119, clone H-300, 1:100), Mucin2 (rabbit, Santa Cruz, sc-15334, clone H-300, 1:100), Foxj1 (mouse, e-bioscience, San Diego, Calif., Cat#14-9965-82, Clone: 2A5, 1:100), cc-10 (goat, Santa Cruz, clone C-20, sc-9770, 1:100), pro-SPC (rabbit, Seven Hills, WRAB-9337, 1:2000), mature SPB (rabbit, Seven Hills, WRAB-48604, 1:1000), Mucin1 (Armenian Hamster, NeoMarkers, Fremont, Calif., Cat#HM-1630-P1ABX, clone MH1, 1:100), Podoplanin (rabbit, Santa Cruz, sc-134482, FL-162, 1:100), AQP5 (goat, Santa Cruz, sc-9890, clone G-19, 1:100). Secondary antibodies were donkey anti-mouse whole IgG-Alexa Fluor 488, 715-545-150, donkey anti-mouse whole IgG-Alexa Fluor 647, 715-605-150, donkey anti-rabbit whole IgG-Alexa Fluor 488, 711-545-152, donkey anti-rabbit whole IgG-Cy3, 711-166-152, donkey anti-goat whole IgG-Alexa Fluor 488, donkey anti-goat whole IgG-Cy3, 705-165-147, donkey anti-goat whole IgG-Alexa Fluor 647, 705-605-147, all from Jackson ImmunoResearch.

The next day, slides were washed with PBS three times, 10 minutes each, followed by incubation with the corresponding secondary antibodies at 1:500 dilutions in 5% fetal donkey serum for 2 hours at RT. The slides were then washed three times with PBS, 10 minutes each. The slides were sealed with DAPI containing mounting solution (IHC world).

Samples were visualized and imaged using motorized Leica DMI 6000B fluorescence microscope coupled with Leica DFC365 EX digital camera and operated by LAS AF 6.2 software (Leica Microsystems GmbH, Wetzlar, Germany). All the pictures were imaged with HCX PL S-APO 10×/NA 0.3 or HCX PL FL L 20×/NA 0.4 objectives. The tile scan images were taken with the image tiling module coupled with autofocus module; and auto-stitched by the LAS AF 6.2 software. The images were exported as JPG files and processed (contrast and brightness adjustments) with Photoshop CS5.1 (New York, N.Y.).

Masson's Trichrome Staining for Collagen in Spheres

The clumps/spheres collected from different time points were preserved in O.C.T and sectioned (5-10 µm/section) using cryostat and were fixed with 10% formalin for 20 minutes at RT and re-fixed in Bouin's solution for 1 hour at 56° C. to improve staining quality. The slides were rinsed in running distilled water for 5-10 minutes to remove yellow color followed by staining in Weigert's iron hematoxylin working solution for 10 minutes. The slides were rinsed in running warm distilled water for 10 minutes followed by staining in Biebrich scarlet-acid fuchsin solution for 10-15 minutes. The slides were washed in distilled water, then differentiated in phosphomolybdic-phosphotungstic acid solution for 10-15 minutes or until collagen was not red. The slides were transferred directly (without rinse) to aniline blue solution and stain for 5-10 minutes followed by a brief rinse in distilled water and differentiation in 1% acetic acid solution for 2-5 minutes. The slides were then washed in distilled water and mounted with resinous mounting media.

Flow Cytometry.

Figure 7:
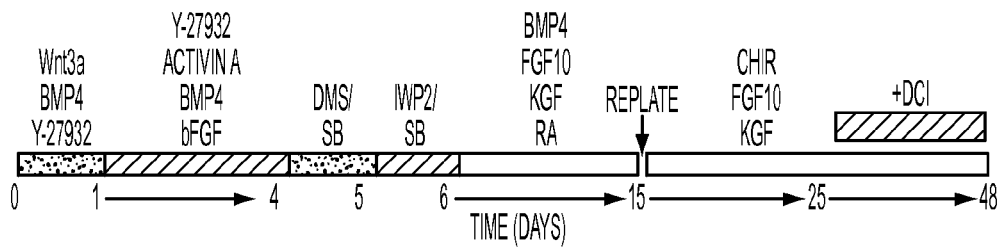
FIG. 7. Flow cytometry. The flow cytometric plots show the uptake of fluorescent recombinant human SPB (BODIPY-SPB) protein by RUES2 cells cultured according to the protocol on top of the panel. Hoechst, a blue nuclei dye that can be taken by live cells, was used as a counterstain to visualize the cells. Top panel, d15 cells; middle panel, d48 cells culture with the addition of CHIR, fgf10, fgf7; bottom panel, d48 cells culture with the addition of CHIR, fgf10, fgf7 and DCI.
Figure 7:
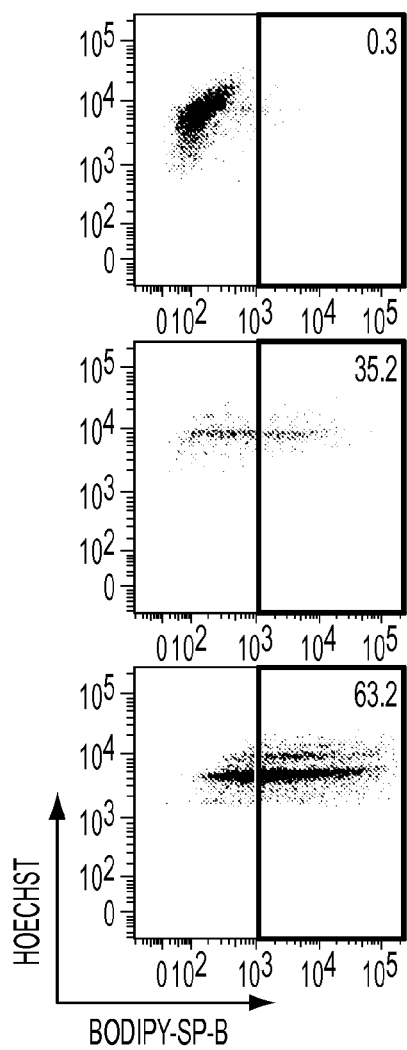

Day 4, 4.5 or 5 embryoid bodies were dissociated into single cells with 0.05% trypsin/EDTA. The cells were stained directly with PE conjugated CXCR4 (Invitrogen) (1:200), and APC conjugated c-KIT (BD Biosciences, San Jose, Calif.) (1:100) in PBS supplemented with 0.1% BSA and 0.2 mM EDTA for 45 min at 4° C. Stained cells were analyzed on a LSRII (BD Biosciences) and results were analyzed by Flowjo software (Tree Star, Ashland, Oreg.). See FIG. 7.

Figure 6A:
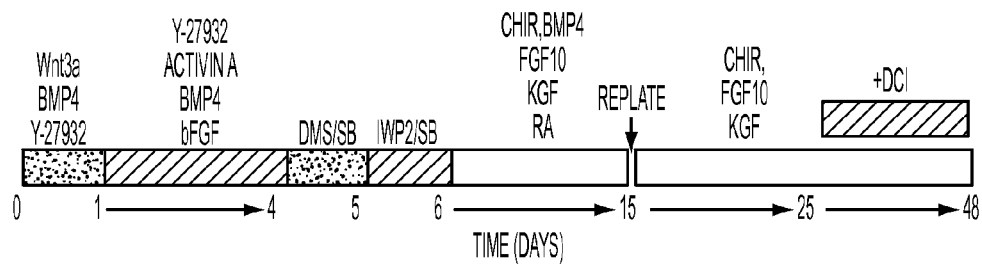
FIG. 6.(a) Culture protocol of RUES2 cells shown in panels (b), (c) and (d). (b) Representative 10× whole culture tile scan of SP-B and SP-C expression inn RUES2 cells cultured according to the protocol shown in (a), without (left) and with (right) addition of DCI at d25. (c) Uptake of BODIPY-SP-B by cells cultured according to the protocol shown in (a). The upper panel (lung progenitors at d15) represents a biological negative control. Immunofluorescence images represent reproducible results from 3 independent experiments. (d) Cellular expansion of RUES2 cells during the culture according to the protocol shown on top of panel (a). (n=4).
Figure 6B:
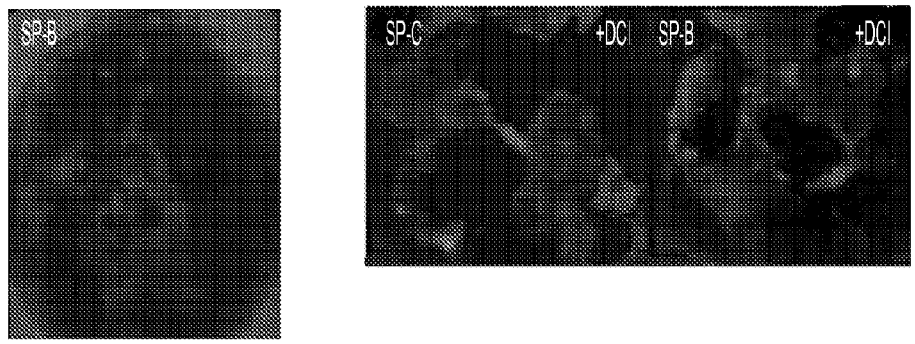
Figure 6C:
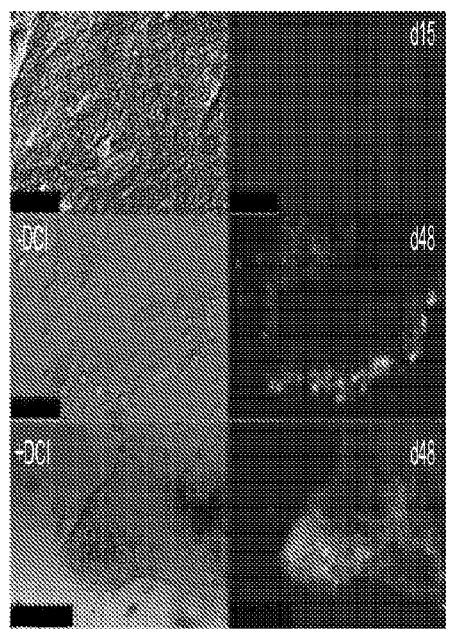

Flow cytometry was also used to isolate alveolar type II cells. A distinguishing functional characteristic of ATII cells is their uptake and recycling of surfactant proteins[48]. Therefore, we added BODIPY-labeled recombinant SP-B. A large fraction of the cells showed uptake of the probe, in particular when cultured in the presence of DCI, while no uptake was observed in lung progenitors at d15 of culture (FIG. 6c). These data indicate that the ATII cells generated in our cultures are functional. We next quantified the fraction of cells that took up SP-B by flow cytometry: only 0.4±0.3% showed detectable uptake at d15, while at d48 17±16% and 52±11% showed uptake in the absence and presence of DCI (P=0.04, n=3), respectively.

General Immunofluorescence Staining

Day-15, -25 or -48 cultures in 48-well tissue culture plates were fixed with 4% paraformaldehyde for 15 minutes at room temperature and washed twice with PBS. The cells were permeabilized in PBS with 0.25% triton and 5% fetal donkey serum (Jackson ImmunoResearch, West Grove, Pa.) for 30 min and blocked in 5% fetal donkey serum for 2 hours at room temperature. The cell cultures were stained with one, or a combination of two or three of the following primary antibodies: FOXA2/HNF-3β (goat, Santa Cruz Biotechnology, Inc., Santa Cruz, Calif., Cat#sc-6554, clone M-20, 1:50), TTF-1/Nkx2.1 (mouse, Invitrogen, 18-0221, clone 8G7G3/1, 1:100), TTF-1/Nkx2.1 (Rabbit, Seven Hills Bioreagents, Cincinnati, Ohio, Cat#WRAB-1231, 1:1000), p63α (rabbit, Santa Cruz, sc-8344, clone H-129, 1:100), Sox2 (Rabbit, stemgent, 09-0024, 1:100), Pax 6 (rabbit, Covance, Princeton, N.J., Cat#PRB-278P, 1:300), Pax8 (mouse, Abcam, Cambridge, Mass., Cat#ab53490, 1:100), EpCAM (APC conjugated, mouse, BD Biosciences, BDB347200), Tuj1 (mouse, Sigma, T8578, Clone 2G10, 1:4000), Mucin5AC (mouse (Biotin), Abcam, ab79082, clone 45M1, 1:100), Mucin5B (rabbit, Santa Cruz, sc-20119, clone H-300, 1:100), Mucin2 (rabbit, Santa Cruz, sc-15334, clone H-300, 1:100), Foxj1 (mouse, e-bioscience, San Diego, Calif., Cat#14-9965-82, Clone: 2A5, 1:100), cc-10 (goat, Santa Cruz, clone C-20, sc-9770, 1:100), pro-SPC (rabbit, Seven Hills, WRAB-9337, 1:2000), mature-SPC (rabbit, Seven Hills, WRAB-76694, 1:1000), mature SPB (rabbit, Seven Hills, WRAB-48604, 1:1000), ABCA3

(rabbit, Seven Hills, WRAB-70565, 1:100), Mucin1 (Armenian Hamster, NeoMarkers, Fremont, Calif., Cat#HM-1630-P1ABX, clone MH1, 1:100), Podoplanin (rabbit, Santa Cruz, sc-134482, FL-162, 1:100), AQP5 (goat, Santa Cruz, sc-9890, clone G-19, 1:100). Secondary antibodies were donkey anti-mouse whole IgG-Alexa Fluor 488, 715-545-150, donkey anti-mouse whole IgG-Alexa Fluor 647, 715-605-150, donkey anti-rabbit whole IgG-Alexa Fluor 488, 711-545-152, donkey anti-rabbit whole IgG-Cy3, 711-166-152, donkey anti-goat whole IgG-Alexa Fluor 488, donkey anti-goat whole IgG-Cy3, 705-165-147, donkey anti-goat whole IgG-Alexa Fluor 647, 705-605-147, all from Jackson ImmunoResearch.

After blocking, all the triple, double or single staining (except "Nkx2.1 (mouse)/p63/FOXA2", "d25 Nkx2.1 (mouse)/Sox2/FOXA2" and "Tuj1/TTF-1/FOXA2") were performed by incubating primary antibody(ies), according to the dilution factors indicated in supplementary table I in staining/wash buffer (5% fetal donkey serum in PBS) at 4° C. overnight (minimum 12 hr), followed by 3×10 min wash. The cultures were then incubated with the corresponding secondary antibodies at 1:300 dilutions in staining/wash buffer at room temperature for 2hr, washed twice for 10 min and incubated with DAPI for 5 min at room temperature. The stained cultures can be preserved in antibiotics supplemented PBS in dark at 4° C. for 2-3 months. The d48 Mucin2, CC-10 SPB and pro-SPC can be preserved up to 6 months or longer. For better maintenance, we preserved the cultures in VECTASHIELD Mounting Media (Vector laboratories, Inc. Burlingame, Calif., Cat#H-1000).

Samples were visualized and imaged using motorized Leica DMI 6000B fluorescence microscope coupled with Leica DFC365 FX digital camera and operated by LAS AF 6.2 software (Leica Microsystems GmbH, Wetzlar, Germany). All the pictures were imaged with HCX PL S-APO 10×/NA 0.3 or HCX PL FL L 20×/NA 0.4 objectives. The tile scan images were taken with the image tiling module coupled with either autofocus or z-stack scanning (1.5 µm/stack) module; and auto-stitched by the LAS AF 6.2 software. The images were exported as JPG files and processed (contrast and brightness adjustments) with Photoshop CS5.1 (New York, N.Y.).

Mice Kidney Capsule Transplantation.

NOD.Cg-PrkdcscidIl2rgtm1Wjl/SzJ (NOD/SCIDIl2rg-/-) mice were purchased from Jackson Laboratory and kept in a specific pathogen-free facility. Experiments and animal care were performed in accordance with the Columbia University Institutional Animal Care and Use Committees (IACUC). Approximately one million cells were injected under the kidney capsule of each mice. Outgrowths were excised, embedded in paraffin or OCT, analyzed using hematoxylin and eosin stains for morphology or immunofluorescence for specific antigens as above.

Quantitative Real-Time PCR

Total RNA was extracted using Trizol (Invitrogen), phase lock tubes (5' Prime) and RNeasy kit (Qiagen, Valencia, Calif.). RNA concentration was measured with a NanoDrop 2000 fluorospectrometer (Thermo Fisher Scientific). RNA quality was verified using an Agilent microfluidic RNA 6000 Nano Chip kit on the 2100 Bioanalyzer (Agilent Technologies, Santa Clara, Calif.). cDNA was generated by reverse transcription of a total of 1 µg RNA with random hexamers and Superscript III [Invitrogen (Life Technologies)] following the manufacturer's instructions. The reaction was carried out in a 20 µL volume. Real-time quantitative PCR was performed on ABI vii7A Thermocycler [Applied Biosystems (Life Technologies)] using ABI Power SYBR Green PCR Master Mix [Applied Biosystems (Life Technologies)]. The Real-time PCR conditions were 50° C. for 2 min and 95° C. for 10 min followed by 40 cycles of 95° C. for 15 s and 60° C. for 1 min, dissociation/melt curves were obtained for each of the genes. Absolute quantification of each gene was obtained using a standard curve of serial diluted genomic DNA and normalized to housekeeping genes β-ACTIN and TBP (Tata Box Binding protein). Quantitative PCR for each sample were performed in triplicates, the input of template per triplicate was cDNA transcribed from 5-10 ng of RNA. Primer sequences are listed in supplementary table II. Any PCR method can be used. Other PCR methods known in the art can also be used.

Live Cell Imaging of Fluorescent-SPB Protein Localization in d48 Cultures

On D15 and 48, differentiation cultures were loaded with 8 µg/ml purified, fluorescent human surfactant protein B (SPB) (BODIPY-SPB) protein in serum-free differentiation (SFD) media, and incubated in a 5% CO2/air environment for 1 hr. Cultures were rinsed twice with SFD and imaged on motorized Leica DMI 6000B fluorescence microscope with HCX PL FL L 20×/NA 0.4 objective.

Statistical Analysis

Statistical analysis was performed using unpaired two-tailed student's t-test. For multiple group comparison (more than two), results were analyzed using one-way analysis of variance followed by Dunnett's multiple comparison test. p-Values<0.05 were considered statistically significant.

Example 2

Maintenance of hPSCs and Induction of Endoderm

RUES2 (Rockefeller University Embryonic Stem Cell Line 2, NIH approval number NIHhESC-09-0013, Registration number 0013; passage 13-24) were cultured on mouse embryonic fibroblasts as previously described[5]. Mouse embryonic fibroblasts were plated at a density of ~30,000 cells/cm$^2$. hPSCs were cultured in a medium of DMEM/F12, 20% knockout serum replacement [Gibco (Life Technologies, Grand Island, N.Y.)], 0.1 mM β-mercaptoethanol (Sigma-Aldrich, St. Louis, Mo.), and 20 ng/ml FGF-2 (R&D Systems, Minneapolis, Minn.). Medium was changed daily and cells were passaged with acutase/EDTA (Innovative Cell Technologies, San Diego, Calif.) every 4-5 days at 1:48 dilution. Cultures were maintained in undifferentiated state in a 5% CO$_2$/air environment. hPSC differentiations were maintained in a 5% CO2/5% O2/95% N2 environment unless indicated elsewhere.

12 hour primitive streak formation and 3 days of endoderm induction were performed in serum-free differentiation (SFD) media [IMDM/Ham F12 (3:1)(Cellgro)] supplemented with N2 [Gibco (Life Technologies)], B27 (Gibco), ascorbic acid (50 µg/ml, Sigma), Glutamax (2 mM, Life Technologies), monothioglycerol (0.4 µM, Sigma), 0.05% bovine serum albumin (BSA) (Life Technologies), 1% penicillin-streptomycin (Thermo Fisher Scientific, Waltham, Mass.), as previously described with slight modification[5]. hPSCs were treated with Acutase (2 min at 37° C.) and plated onto Matrigel (BD Bioscience) coated 10 cm tissue culture dish (1:2 dilution) for 24 hr to deplete residual mouse embryonic fibroblasts. Cells were then briefly trypsinized (0.05%, 1 min at 37° C.) into small cell clumps containing 3-10 cells and plated onto low attachment 6-well plates [Costar (Corning Incorporated, Tewksbury Mass.)] (1:1 dilution) to form embryoid bodies. For primitive streak formation, Wnt3a 10 ng/ml, Y-27632, [10 µM, Tocris (R&D Systems)] and human BMP4, (3 ng/ml, R&D Systems) were added in the media for 12 hr. Embryoid bodies were then collected, resuspended in endoderm induction media containing Y-27632 (10 µM), human BMP4 (0.5 ng/ml), human bFGF, (2.5 ng/ml, R&D Systems), human ActivinA, 100 ng/ml (R&D Systems) for 72 hrs on low-adherence plates. Cells were fed every 24 hrs (depending on the density) by removing half of the old media and adding half fresh media.

Example 3

Induction of Anterior Foregut Endoderm

For anterior foregut endoderm induction, day 4 embryoid bodies were dissociated into single cells using 0.05% Trypsin/EDTA [cellgro (Corning)] for 2-4 mins. The endoderm cells were plated on fibronectin-coated (Sigma) 48-well tissue culture plates (75,000 cells/well) in SFD media supplemented with 100 or 200 ng/mL of the BMP inhibitor Noggin (R&D) and 10 µM the TGF-beta inhibitor SB431542 (SB) [Tocris (R&D Systems)] for 24 hr. In another embodiment 1.5 µM of the BMP inhibitor Dorsomorphin dihydrochloride (DSM) (Tocris, R&D) is used instead of Noggin.

On day 5, the media was switched to SFD supplemented with 10 µM SB431542 (TGF-beta inhibitor) and 1 µM IWP2, a Wnt signaling inhibitor [Tocris (R&D Systems)] [Tocris (R&D Systems for another 24 hrs. Longer incubations that one day can be used here, and any Wnt signaling inhibitor can be used. After incubation with the Wnt inhibitor, the cells can be used to generate spheres of lung and airway epithelial cells as is described below.

In some experiments, the AFE were specified by 48 hr of Dorsomorphin (1.5 µM) and SB431542 (10 µM) treatment only, without switching to SB431542 and IWP2. This condition was less efficient (20% lower) in lung induction than Dorsomorphin/SB431542 and IWP2. that induces the endoderm to commit to liver fate (which is a posterior foregut endoderm organ) were also tested.

Hepatic conditions contain BMP-4, 50 ng/ml; HGF, 10 ng/ml; dexamethasone, 40 ng/ml; bFGF, 10 ng/ml; VEGF, 10 ng/ml; TGFα, 20 ng/ml; murine EGF, 20 ng/ml (All from R&D, except dexamethasone from Sigma)[5,13]. The liver/hepatic condition is used as a negative control for mRNA expression and protein expression analysis, as the lung markers are not expression in hepatocytes. Any method for making DE or enriched populations of AFE known in the art can be used in the present embodiments.

The AFE cells produced as described above, also herein referred to as DE cells) can be used at this point to make lung and airway epithelial cells. AFE can also be used as starting material to create spheres of lung and airway progenitor cells.

Example 4

Induction of FOXA2+NKX2.1+ Lung Progenitors

For d6-15 lung progenitor induction (9 days), the AFE from Example 3 were treated with a 'ventralization' cocktail containing CHIR99021, 3 µM (WNT signaling agonist), human FGF10, 10 ng/ml; human FGF7, 10 ng/ml; human BMP4, 10 ng/ml; murine EGF, 20 ng/ml and all-trans retinoic acid (ATRA), 0-1 µM (all from R&D, except CHIR99021 from (Stemgent, Cambridge. Mass.) and ATRA from Sigma) in SFD media for 8-10 days. This treatment produced lung and airway progenitor cells (also herein referred to as "lung field progenitor cells"). At this stage, the lung progenitor cells were early, and they might have committed to a lineage of either lung or airway epithelium, but we wouldn't be able to know because the corresponding airway and distal lung specific markers are not expressed at this stage yet.

For RUES2 differentiation, the d8-15 cultures were maintained in a 5% CO2/air environment.

For SViPS differentiation, the d12-15 cultures were maintained in a 5% CO2/air environment.

To examine the contribution of each of the factors to the specification of lung and airway progenitors, each of the factors was withdrawn from the 'ventralization' cocktail (i.e., CHIR99021, FGF10, FGF7, BMP4 and EGF), or blocked by specific inhibitors (i.e., NOGGIN as biological inhibitor of BMP4 signaling and IWP2 as pharmacological inhibitor of WNT signaling), or added at different concentrations (i.e., RA 0, 0.05, 0.1, 0.5, 1 µM, and BMS493 (10 µM, Tocris) as RA inhibitor). Based on these experiments it was determined that AFE need only be treated with a Wnt signaling agonist, RA and an agent that activates BMP4 signaling or BMP4 for at least 9 days in order to be induced to differentiate into lung and airway progenitor cells. The other factors including fibroblast growth factors (FGFs) and epidermal growth factors (EGFs) are optional, however, the addition of one or two or three of these other factors helps cell growth. For example, the lung and airway cells generated with the addition of FGF (during day 6-15 of the example) could grow better post day 15.

Results

It was previously shown that highly enriched AFE can be induced by first specifying DE, followed by blocking BMP and TGF-β signaling[5]. DE is induced using established protocols[9-12] for 4.5 days (see FIG. 1a) resulting in embryoid bodies that are highly enriched (>90% as judged by expression of EPCAM, CXCR4 and c-KIT[12,13]) in DE. DE is the starting material for the embodiments of the present invention.

To make the progenitor cells DE was exposed in monolayer cultures to inhibitors of BMP and TGF-β signaling (the anteriorization stage), giving rise to "highly enriched AFE (FOXA2+SOX2+CDX2−)." Application of a 'ventralization cocktail' consisting of factors involved in dorsoventral patterning of the AFE, including a Wnt agonist, FGF10, KGF, BMP4 and EGF,[14-18] as well as a factor important for lung bud development, retinoic acid (RA) (WFKBE+RA)[19] yielded NKX2.1+FOXA2+ lung and airway progenitor cells, (also referred to as lung and airway field cells that were devoid of the thyroid marker PAX8 and the neural marker PAX6, and corresponded to the lung field of the AFE[5]. However, in the aforementioned culture protocol[5], the enrichment in lung field cells (NKX2.1+FOXA2+)[3] never exceeded 35-40%, and expression of specific lung and airway epithelial markers was absent.

Although the "highly enriched AFE (FOXA2+SOX2+CDX2−)" can be exposed a simpler cocktail of Wnt agonists, BMP4 or an agent (including small molecules) that activate BMP4 signaling, and RA, adding growth factors such as FGF is advised if the cells need to be cultured longer than 25 days, since FGF helps for the growth of endodermal cells.

To improve efficiency the AFE induction method was refined. In the mouse embryo, DE cells fated to become AFE pass through a zone where the Nodal/Activin inhibitor Lefty and the BMP4 inhibitor Noggin are expressed[20,21], likely explaining why blocking TGF-β and BMP signaling is important for AFE specification. Subsequently, the cells are exposed to the Wnt inhibitor, Dkk1[22], suggesting a role for Wnt inhibition in AFE development. We have shown previously that simultaneous blocking of BMP, TGF-β and Wnt signaling is detrimental to AFE formation from hPSCs[5]. Therefore, we examined the effect of sequential inhibition of these pathways.

After DE induction, the cells were dissociated, replated on fibronectin-coated plates and exposed sequentially between days d4.5 to d6.5 to combinations of small molecule inhibitors of BMP (dorsomorphin (DSM)[23]), TGF-β (SB431542 (SB)[24]) and WNT (IWP2 (I)[25]) signaling (FIG. 1a). These cells were then cultured in the presence of the ventralization cocktail that contained CHIR99021 (a small molecule Wnt agonist, CHIR99021 is a GSK inhibitor that mimics WNT signaling)[26], FGF10, KGF, BMP4 and RA (0.1 M) (CFKB (CHIR99021, FGF10, KGF, BMP4) +RA) until d15. Compared to exposure to DSM/SB, addition of DSM/SB from d4.5 to 5.5 followed by SB/I from d5.5 to d6.5 increased the fraction of NKX2.1$^+$FOXA2$^+$ cells (from 51.2±2.7 to 70.1±2.1%, P=0.004, n=3) and of NKX2.1 mRNA (FIG. 1a) at d15. Reversing the DSM/SB->SB/I sequence to SB/I->DSM/SB or using SB/I alone was detrimental for NKX2.1 protein expression (22.0±4.8% and 18.8±5.0% NKX2.1$^+$FOXA2$^+$ cells, respectively) and mRNA expression (FIG. 1a). These results indicated that AFE generation through sequential inhibition of BMP and TGF-β, followed by TGF-β and WNT inhibition improved subsequent lung specification.

It has been shown previously that the duration of DE induction by Activin A also determines its subsequent potential to develop into the pancreatic lineage[11]. Therefore, experiments were conducted to determine to what extent the duration of DE induction in the presence of Activin A determines its subsequent lung potential.

Figure 1B:
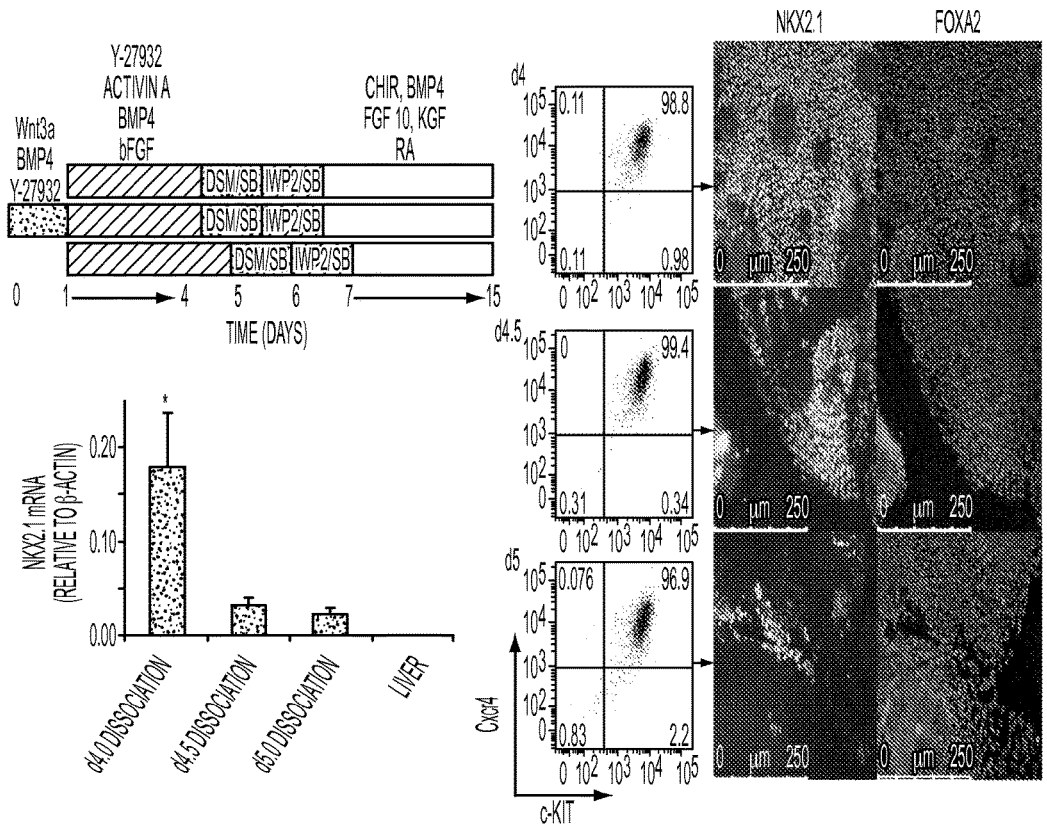
Figure 8:
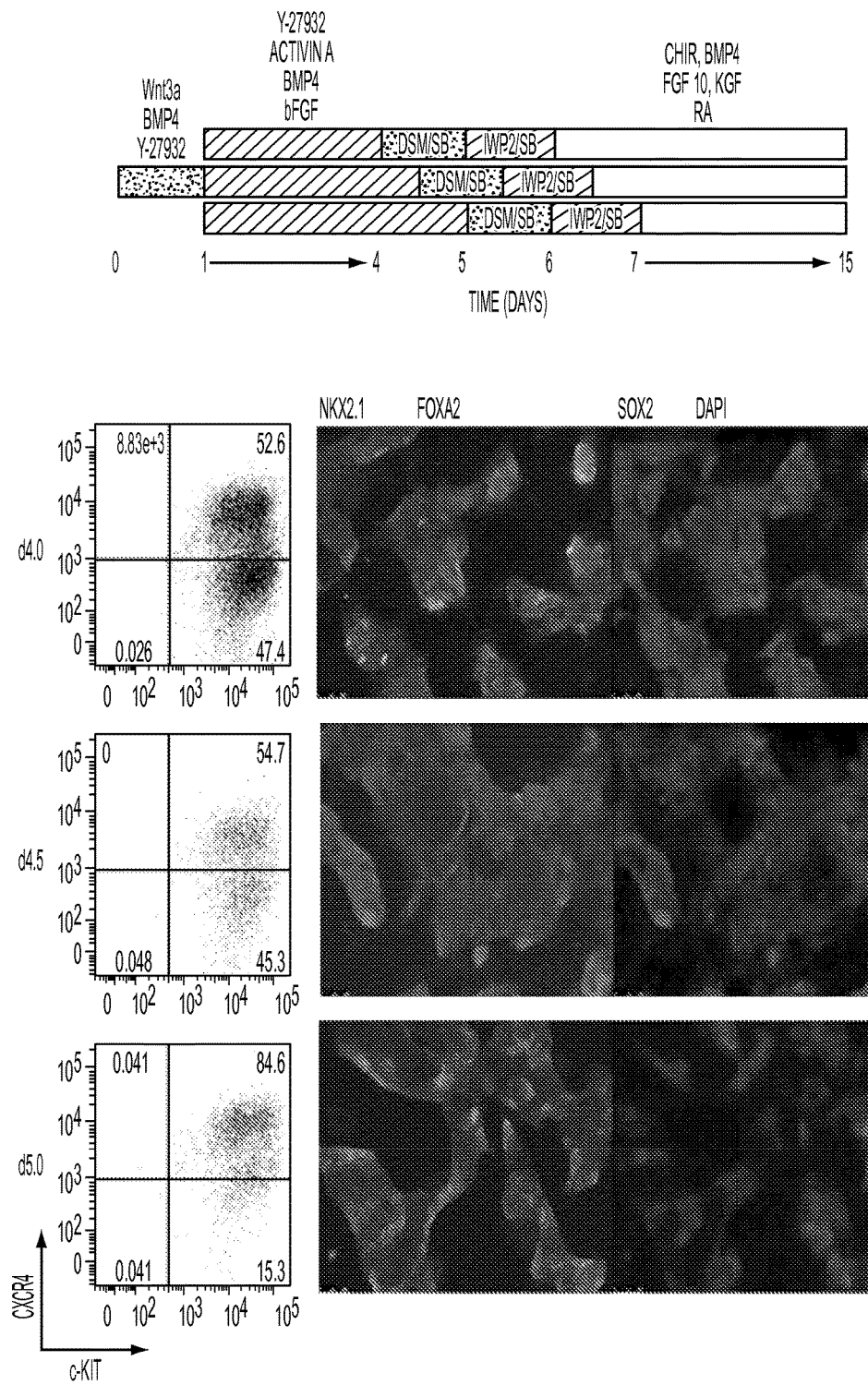
FIG. 8. Effect of duration of endoderm induction on expression of NKX2.1, SOX2 and FOXA2 in sviPS cells at d15 of the differentiation protocol shown on top of the panel. The flow cytometric plots and immunofluorescence images represent reproducible results from 3 independent experiments.
Figure 10:
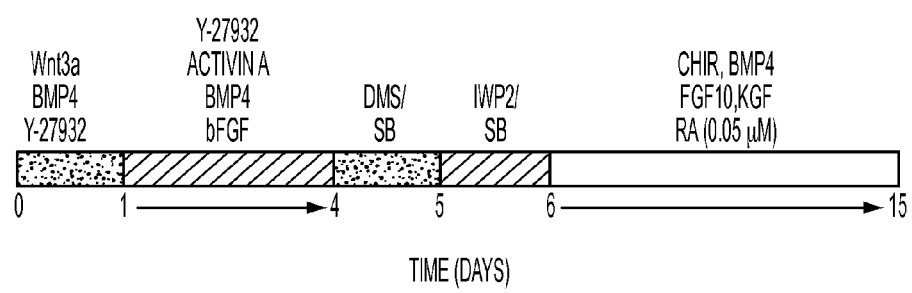
FIG. 10. High magnification view of the expression of SOX2 and NKX2.1 in sviPS cells cultured according the protocol shown on top of the figure. Note the expression of NKX2.1 in areas of low SOX2 expression and vice versa.
Figure 10:
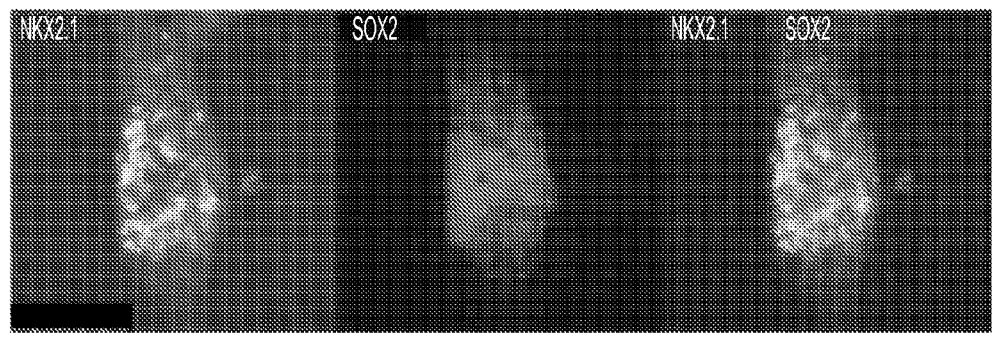

The potential to generate NKX2.1$^+$FOXA2$^+$ cells in the RUES2 line was the highest when DE was induced for 4.0 days, became limited when DE was induced for 5 days (FIG. 1b), and was absent at d6 (not shown). However, in an iPS line generated using Sendai virus (sviPS)[27], where the efficiency of DE induction was invariably lower than in RUES2 cells (FIG. 8, FIG. 1b), the best DE induction time was 5.0 days (FIG. 8). Optimization of the generation of lung progenitors therefore requires optimizing the duration of DE induction in embryoid bodies (EBs) for each cell line, using routine methods known in the art. Even so, a smaller fraction (approximately 25%) of the cells expressed NKX2.1 in sviPS than in RUES2 cells, although most cells in the culture were FOXA2$^+$SOX2$^+$, indicative of efficient AFE induction (FIG. 8). Interestingly, in these cultures, cells expressing NKX2.1 expressed lower levels of SOX2 than cells negative for NKX2.1 (FIG. 10). During dorsoventral patterning of the AFE, SOX2 expression is higher dorsally and in the esophagus than ventrally and in the trachea[3]. It is possible that the FOXA2$^+$NKX2.1$^-$SOX2$^{bright}$ cells in these cultures are specified towards an esophageal fate. In another iPS line generated by mRNA transfection[28], the efficiency of lung field induction approached 80% (not shown). This is likely a reflection of the well-documented inherent variability in the efficiency of differentiation of individual ES[29, 30] and iPS lines[31, 32] into a given lineage.

Figure 2A:
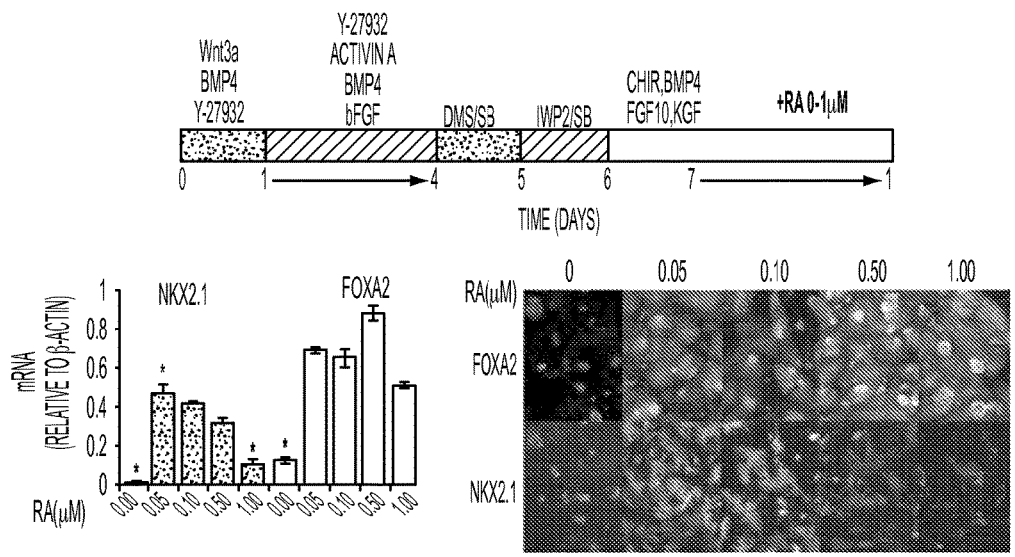
FIG. 2.(a) Expression of NKX2.1 and FOXA2 mRNA (lower left) and protein (lower right) after culture of RUES2 cells according to the protocol on top of the panel using various concentrations of RA during the 'ventralization' stage. Triplicate experiments representative of 3 independent experiments, *, P<0.05, compared with 0.5 µM RA group. (b) 10× tile scan of 25 (5×5) contiguous fields showing expression of FOXA2, SOX2 and NKX2.1 in RUES2 cells cultured according to the protocol on top of the panel. (c) 20× tile scan of 4 (2×2) contiguous fields showing expression of TUJ1, NKX2.1 and FOXA2.1 in RUES2 cells cultured according to the protocol on top of panel (b). (d) 20× tile scan of 4 (2×2) contiguous fields showing expression of p63, NKX2.1 and FOXA2.1 in RUES2 cells cultured according to the protocol on top of panel (b). Immunofluorescence images from FIG. 2a-d represent reproducible results from 3 independent experiments.
Figure 9A:
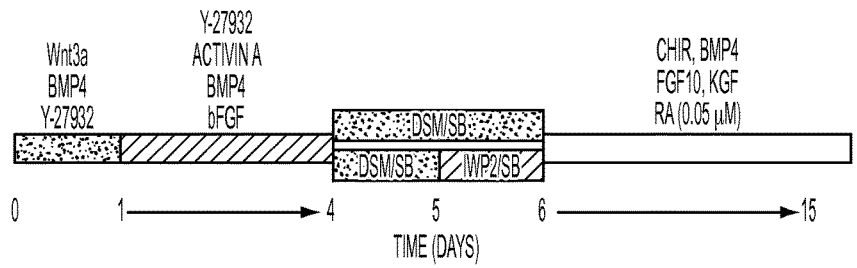
FIG. 9. The culture condition protocol is shown as (a). (b) Expression of NKX2.1, PAX1, PAX8, TG (thyroglobulin) and TSHR mRNA at d15 in the two culture conditions shown on top of the figure. Triplicate experiment, representative of 3 independent experiments. 'Liver' represents DE cultured in the presence of BMP4 and bFGF, which specifies hepatic fate19. The inset shows the expression of PAX8, TG and TSHR mRNA on a recalibrated Y-axis. (c) Expression of NKX2.1 and FOXA2 after culture of RUES2 cells according to the protocol on top of FIG. (a).
Figure 9B:
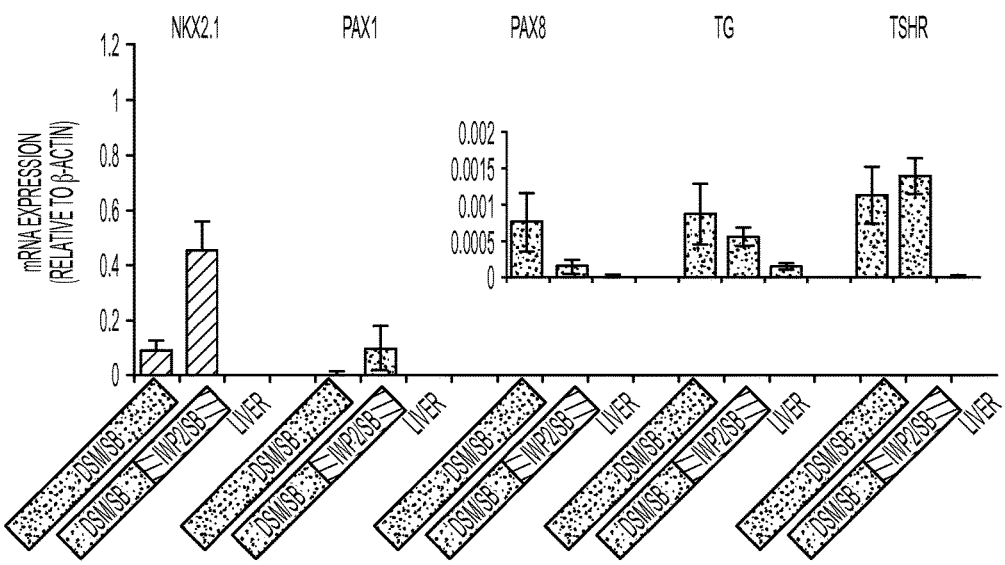
Figure 9C:
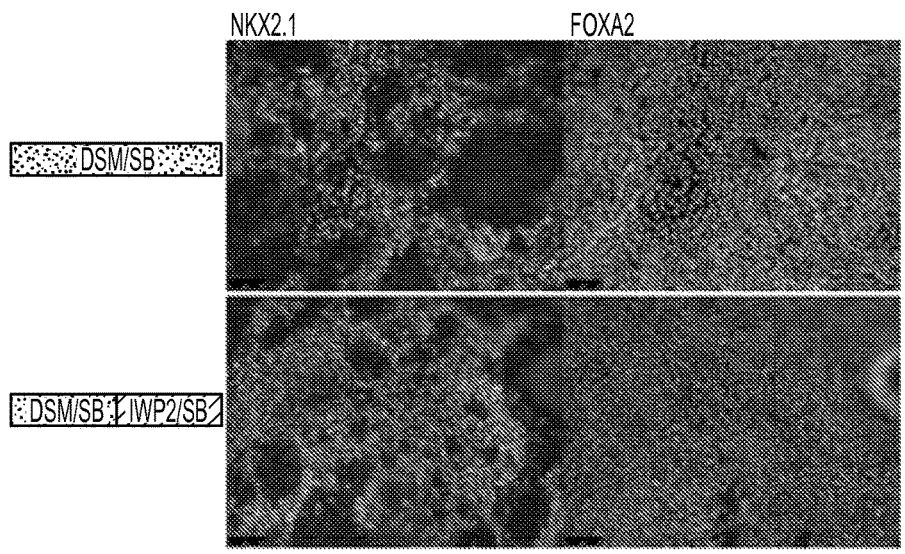

Experiments were designed to optimize the concentration of RA in the 'ventralization' cocktail (FIG. 2a). In the absence of RA, FOXA2$^+$ endoderm was not maintained. At low RA concentrations (0.05-0.1 μM), optimal induction of NKX2.1 and FOXA2 mRNA and protein was observed. At higher RA concentrations, FOXA2$^+$ endoderm was maintained, but NKX2.1 mRNA and the NKX2.1$^+$ fraction (FIG. 2a) dropped. In these conditions, too, AFE induction in the presence of DSM/SB->IWSP2/SB was consistently superior to DSM/SB for the generation of NKX2.1$^+$FOXA2$^+$ cells at d15 (FIG. 9a,b).

Figure 2B:
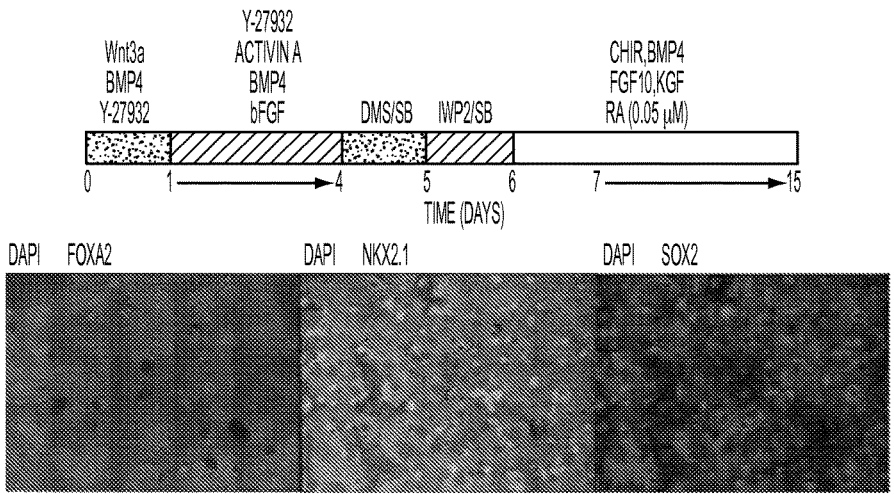
Figure 2C:
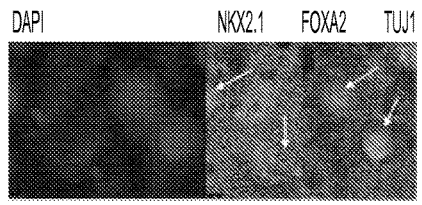
Figure 11:
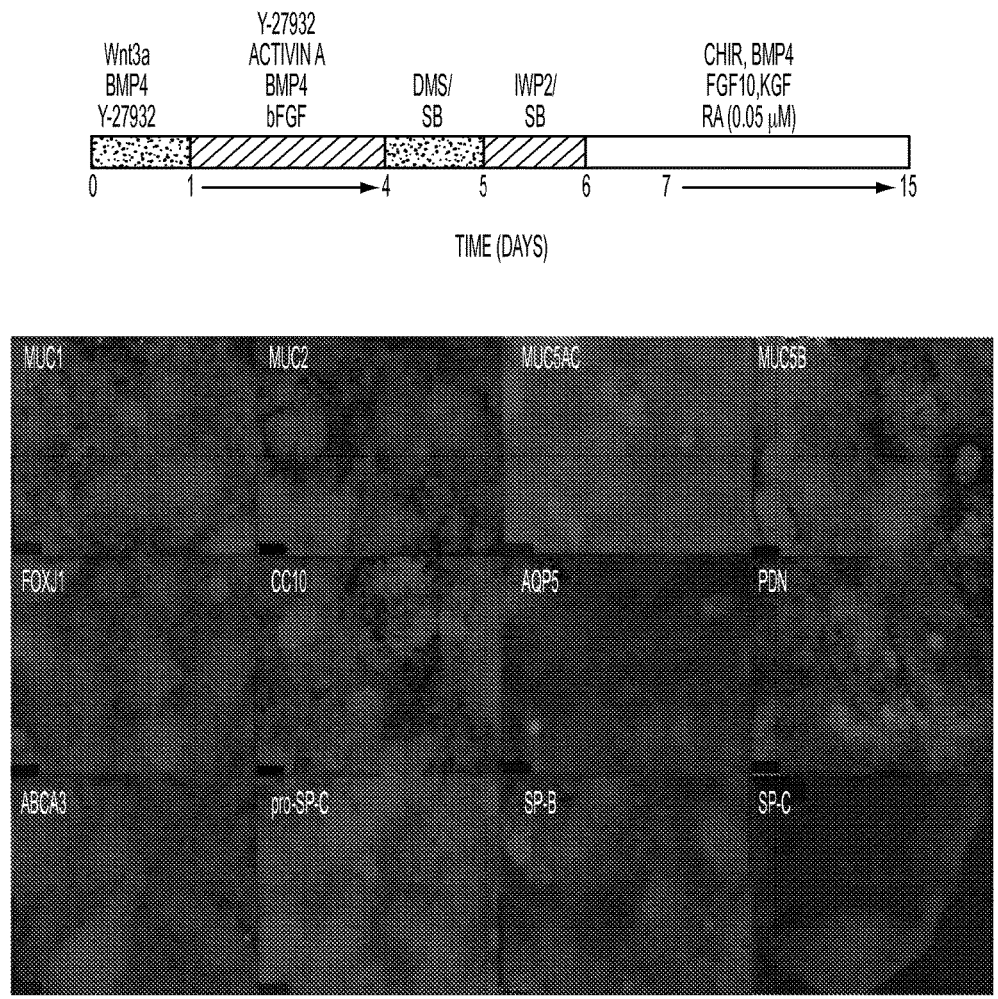
FIG. 11. Representative example of the (absent) expression of markers of mature lung and airway epithelial cells after culturing RUES2 cells according to the protocol shown on top of the figure. Results representative of 4 independent experiments.

These manipulations resulted in cultures where ~95% of the cells were FOXA2$^+$, 80-90% of which expressed NKX.2.1 (FIG. 2b). No markers for any type of mature lung epithelial cells (goblet cells (MUC1, MUC2, MUC5AC, MUC5B), ciliated cells (FOXJ1), Clara cells (CC10, SCGB3A2), ATII cells (pro-SPC, SP-B, ABCA3), ATI cells (PDN, AQ5)) were detected by immunofluorescence, however (FIG. 11).

Figure 2D:
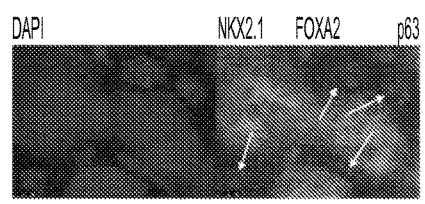

The cultures were analyzed for contaminating lineages. No qPCR or immunofluorescence evidence for thyroid differentiation (PAX8, TG, TSHR) was observed (not shown, and FIG. 9a). This is important as NKX2.1 is also expressed in thyroid[7, 33]. However, two types of contaminating cells occurred. Clusters of FOXA2$^{bright}$NKX2.1$^-$ cells that stained weakly for the neural marker TUJ1 (FIG. 2c, arrows), but not for PAX6 (not shown) were observed. This phenotype is suggestive of midbrain floorplate neuronal precursors. Neural floorplate generation requires dual BMP and TGF-β inhibition, followed by Wnt and sonic hedgehog (SHH) agonism[34]. Taking into account that AFE expresses SHH[35], it is likely that these cells are derived from remaining pluripotent cells after DE induction. In addition, islands of cells expressing the epithelial progenitor marker p63 were observed (FIG. 2d, arrows). As these cells were NKX2.1$^-$ FOXA2$^-$ (FIG. 2f, arrows) and SOX2$^-$ (not shown) they are not endodermal progenitors. The cells were also negative for neuronal markers (not shown). Their identity is unknown.

Figure 3:
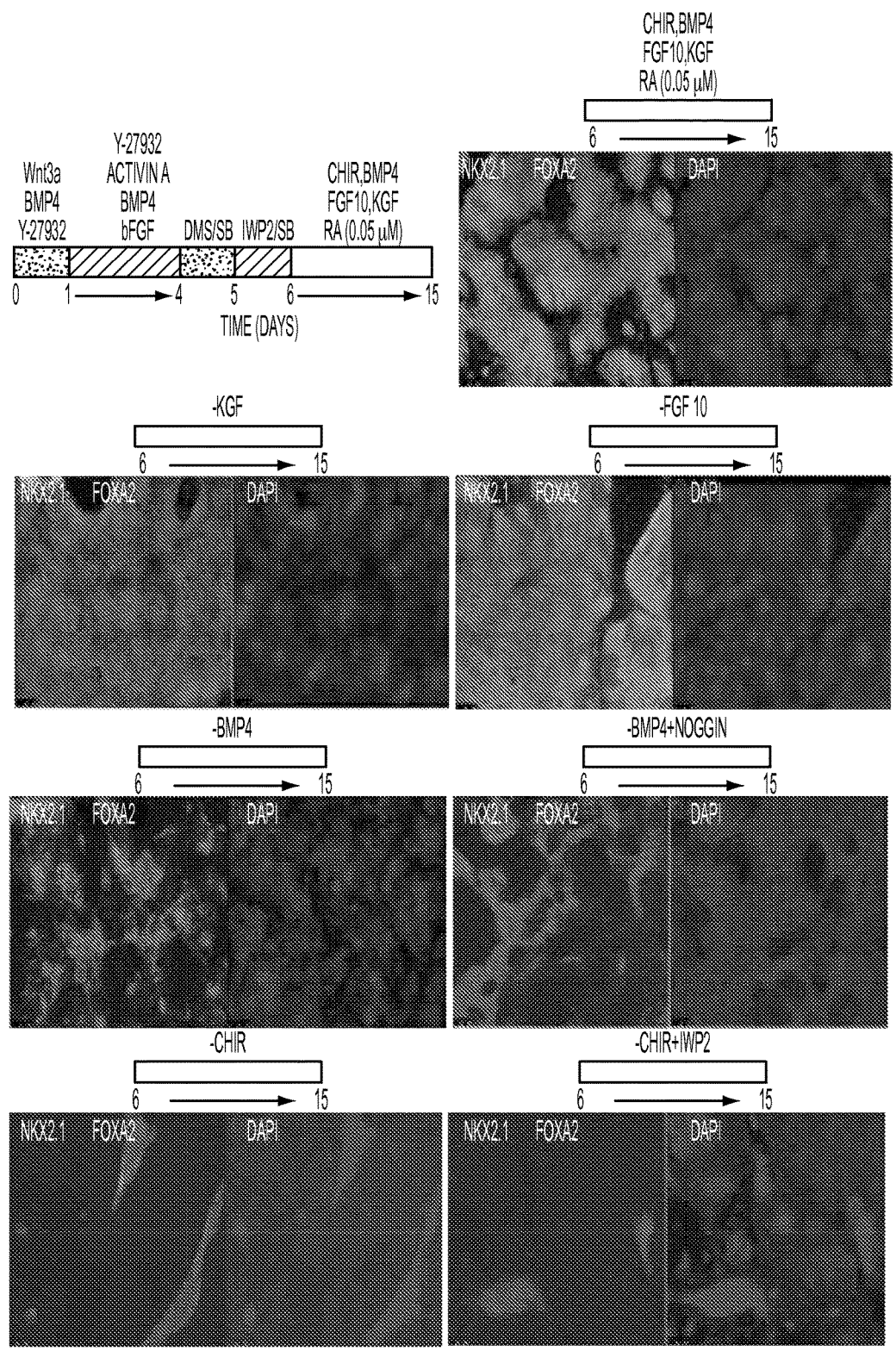
FIG. 3. Effect of removing individual factors or blocking signaling pathways during the 'ventralization' stage (d6-d15) on the expression of FOXA2 and NKX2.1 in RUES2 cells cultured according to the protocol shown on the upper right of the figure. 10× tile scans of 9 (3×3) contiguous fields. Immunofluorescence images represent reproducible results from 3 independent experiments.

Experiments were conducted to determine whether AFE generated after the DSM/SB>SB/I anteriorization stage could respond to known inducers of a lung fate identified in the mouse, as indicated by NKX2.1 expression. We next removed each individual factor from the CFKB cocktail (FIG. 3). Removing either FGF10 (FIG. 3), FGF7 (FIG. 3) or both (not shown) had no effect, suggesting that endogenously produced FGFs are sufficient, or that FGF signaling is dispensable in the human system. However, removing BMP4 reduced the generation of NKX2.1$^+$ cells to approximately 40% (FIG. 3), while blocking BMP signaling by the addition of NOGGIN severely impaired the generation of FOXA2$^+$NKX2.1$^+$ cells to less than 5%. Removing the WNT agonist (mimetic) CHIR severely reduced the generation FOXA2$^+$ and FOXA2$^+$NKX2.1$^+$ cells, while additional blockade of endogenous WNT signaling by IWP2 completely abrogated the generation of NKX2.1$^+$ cells (FIG. 3). These data correspond to findings in mouse genetic models. Wnt signaling is important for the induction of the lung buds[14, 36]. BMP4 is expressed in the mesenchyme surrounding ventral AFE, while Noggin is expressed dorsally[3, 14, 18, 37]. Conditional inactivation of BMP receptors in the AFE[17] as well as deletion of BMP4 in the AFE and surrounding mesoderm[18] led to tracheal agenesis and abnormal lung development, which could not be rescued by increased Wnt signaling[17]. Thus the progenitors generated with the herein described procedure represent an in vitro model that behaves in a fashion consistent with mouse lung development in vivo.

To summarize, these results led to a simplified and yet optimal protocol for making lung and airway progenitors that includes: (a) culturing DE in a TGF-beta inhibitor and a BMP inhibitor for at least 1 day, (b) culturing the cells of step (a) in a Wnt signaling inhibitor and a TGF beta inhibitor for at least one day, and then; (c) culturing the cells of step (b) in a Wnt signaling agonist, RA and an agent that activates BMP4 signaling or BMP4 for at least 9 days thereby producing lung and airway progenitor cells.

Example 5

In Vitro Differentiation of NKX2.1+FOXA2+ Cells into Cells Expressing Markers of Lung and Airway Epithelial Lineages On day 15/16, the lung field progenitor cells were replated after brief trypsinization onto fibronectin-coated plates at 1:5 dilution. The cells were incubated in 0.05% warm trypsin/EDTA for 1 min. Trypsin was then removed by suction and wash media (IMDM+5% FCS) was added into the well, and the cell clumps were gently removed off the plate using 1 ml pipet tips and transferred to a 15 ml tube. After gently mixing with 1 ml pipet tips, the clumps were allowed to settle for 2 minutes. Supernatant (containing single cells and small clumps of cells (<10 cells/clump)) was removed. The remaining cell clumps were replated into fibronectin-coated plates at 1:5 dilutions (it is preferable to replate large clumps) in the presence of serum free differentiation medium (SFD) containing either a combination of 5 factors (CHIR99021, 3 µM; human FGF10, 10 ng/ml; human FGF7, 10 ng/ml; human BMP4, 10 ng/ml; and ATRA, 50 nM), or three factors (CHIR99021, 3 µM, human FGF10, 10 ng/ml; human FGF7, 10 ng/ml).

D15-25 cultures were maintained in a 5% CO2/air environment. From d25 to d48, cultures were carried further in either of these two conditions, with or without the addition of maturation components referred to herein as DCI containing 50 nM Dexamethasone, 0.1 mM 8-Bromo-cAMP (Sigma), and 0.1 mM IBMX (3,7-Dihydro-1-methyl-3-(2-methylpropyl)-1H-purine-2,6-dione) (Sigma)[47].

It was next determined whether these lung progenitors differentiate further. BMP4, FGF10, KGF, Wnt, and RA play a role in the differentiation of respiratory epithelium[14-16, 18, 38-42]. However, upon initiation of branching morphogenesis in mouse embryos, RA signaling decreases in the most distal section of the developing lung[41]. Furthermore, constitutively active RA signaling prevents distal lung development, and favors proximal airway development[42]. The role of BMP signaling is controversial and model-dependent[17, 38]. It has been shown that removal of BMP4 from the growth factor cocktail favored the expression of SFTPC (SP-C) mRNA, though pro-SP-C protein was not detected[5]. Therefore, subsequent experiments were focused mostly on cells cultured in the presence of CFK.

Figure 4A:
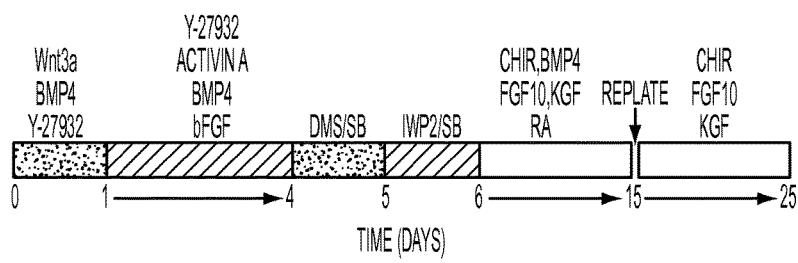
FIG. 4.(a) Culture protocol of RUES2 cells shown in panels (b), (c) and (d). (b) and (c) 10× tile scans of the expression of p63, SOX2 and NKX2.1 in representative colonies obtained after culturing RUES2 cells according to the protocol shown in (a). (d) Expression of p63 and MUC5AC after culturing RUES2 cells according to the protocol shown in panel (a). Immunofluorescence pictures represent reproducible results from 4 independent experiments.
Figure 4B:
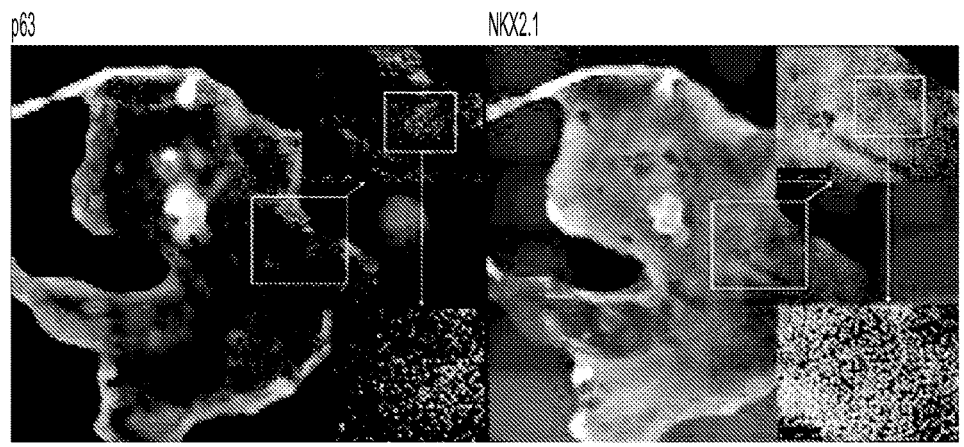
Figure 4C:
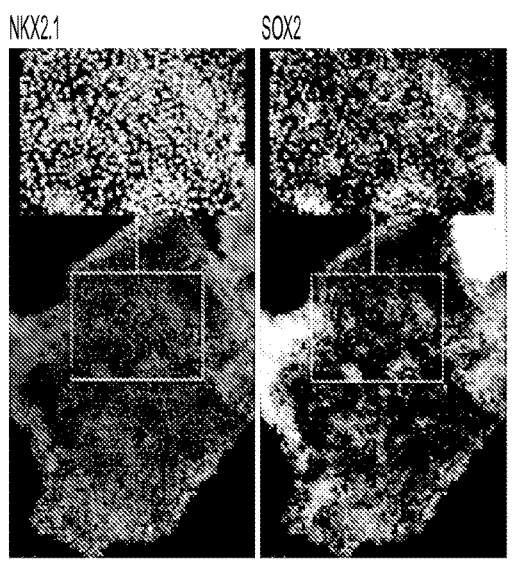
Figure 4D:
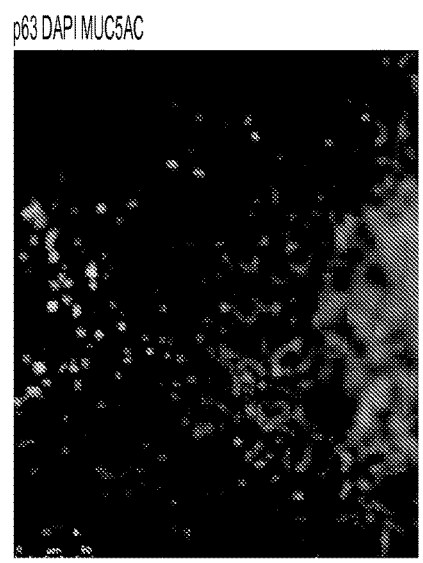
Figure 5:
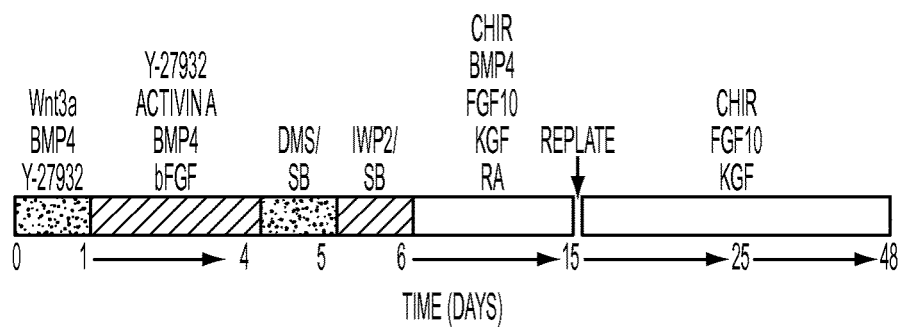
FIG. 5. Representative examples of the expression of markers of mature lung and airway epithelial cells after culturing RUES2 cells according to the protocol shown on top of the figure. Immunofluorescence images represent reproducible results from 4 independent experiments.
Figure 5:
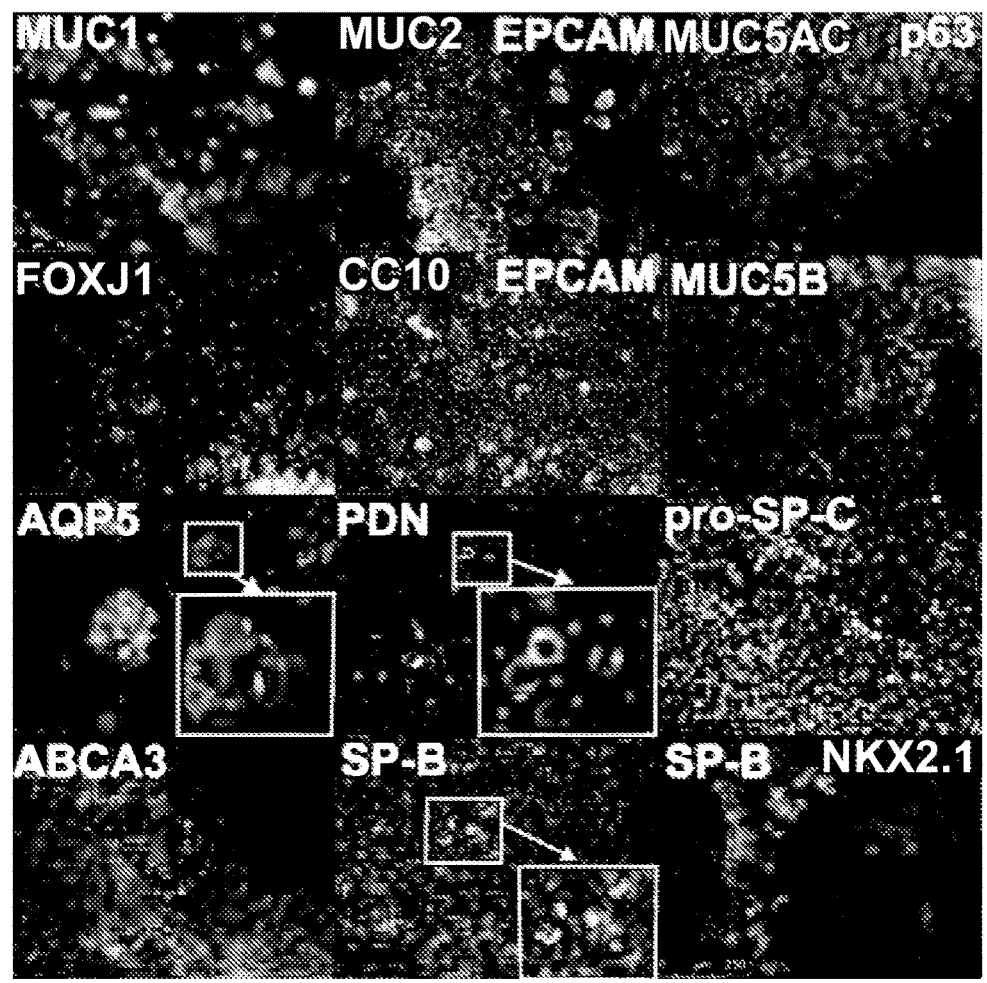
Figure 12:
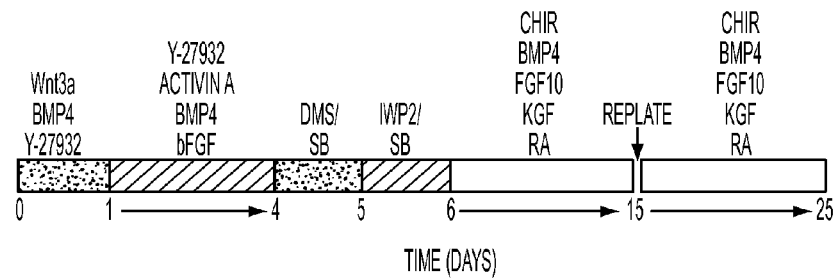
FIG. 12. Expression of NKX2.1, FOXA2, SOX2, P63 and MUC5AC in representative colonies obtained after culturing RUES2 cells until d25 according to the protocol shown on top of the figure. Results representative of 3 independent experiments.
Figure 12:
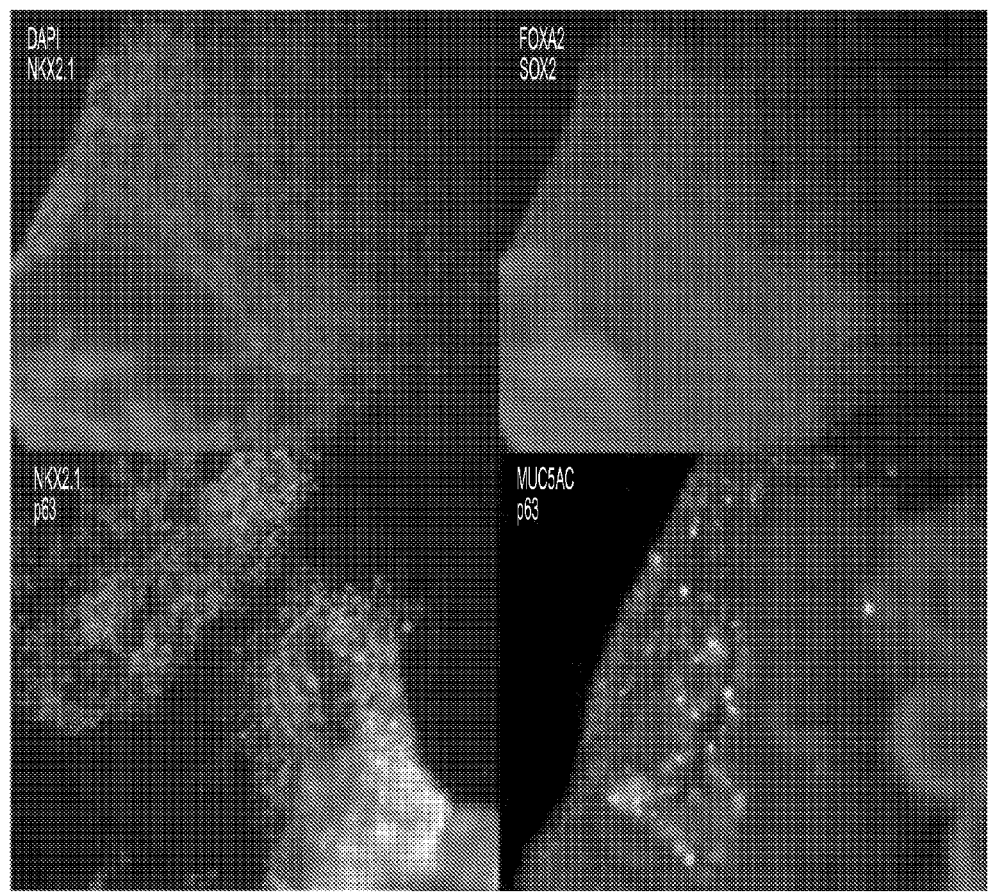

Lung-specified AFE lung and airway progenitor cells at d15 were replated in the presence of CFK after mild trypsinization, brief sedimentation, and collection of larger cell clumps for replating (FIG. 4a). Preliminary experiments indicated that these were depleted of P63+FOXA2−NKX2.1− cells and of neural elements, which were present in smaller aggregates in the supernatant or remained attached (not shown). In these cultures, cells grew as large colonies that were positive for NKX2.1 and SOX2 at day 25 (FIG. 4b,c), and contained p63+NKX2.1+ cells, suggestive of basal cells (these are airway cells), the stem cells of the large airways[43] at the periphery (FIG. 4b,d). Within the colonies, sporadic expression of MUC5AC (FIG. 3d) was detected (FIG. 4d). These staining patterns were also observed in cells cultured in the presence of CFKB+RA (FIG. 12). No other markers of respiratory (lung and airway) epithelial cells were detected at d25 at the protein level by immunofluorescence (not shown).

Figure 13:
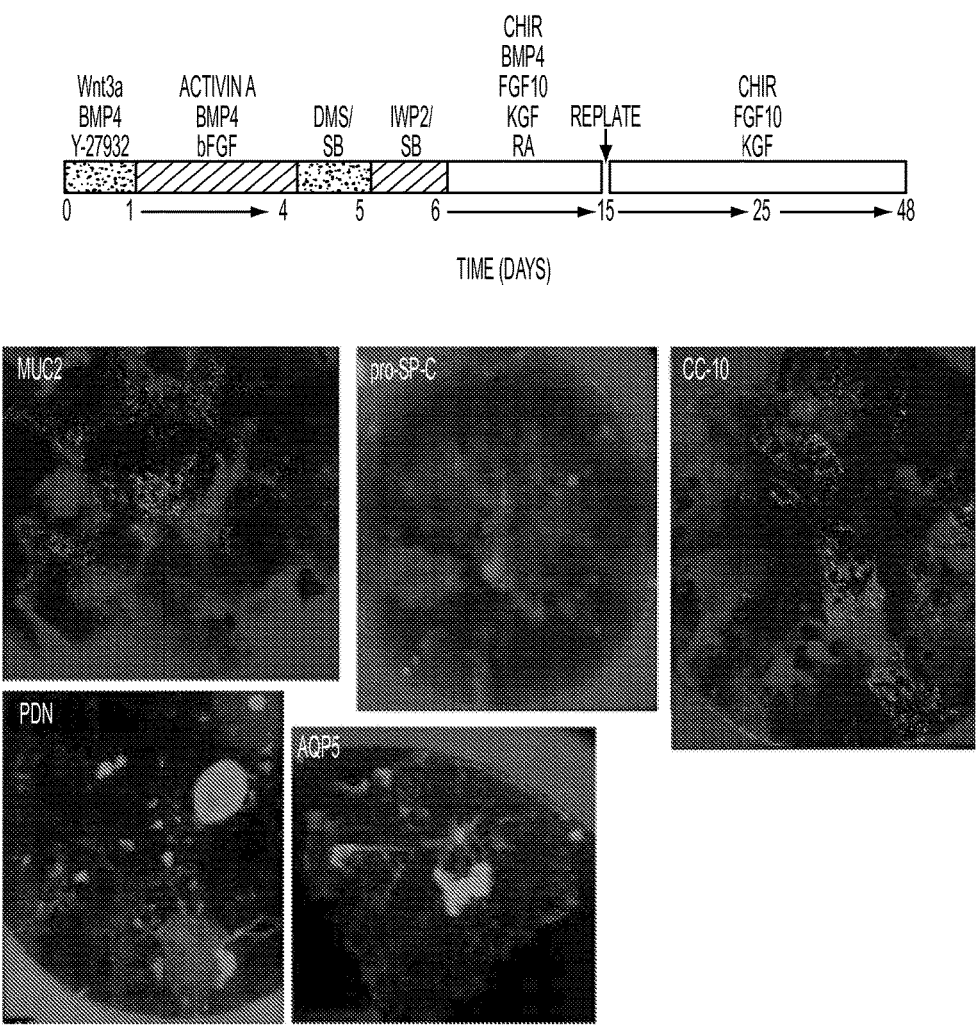
FIG. 13. Representative 10× whole culture tile scans of RUES2 cells cultured according to the protocol shown on top of the figure. The densely pink areas in the PDN and AQP5 stains are staining artifacts.

Cultures at d48 were stained for a variety of lineage-specific markers (FIG. 5; tile scans are shown in FIG. 13; data from sviPSCs are shown in FIG. S7). To reliably establish expression of lineage-specific markers, d15 cultures, where stains were performed with the same antibodies and images were acquired using the same settings, served as biological negative controls (see FIG. 11 for a representative example).

Figure 14:
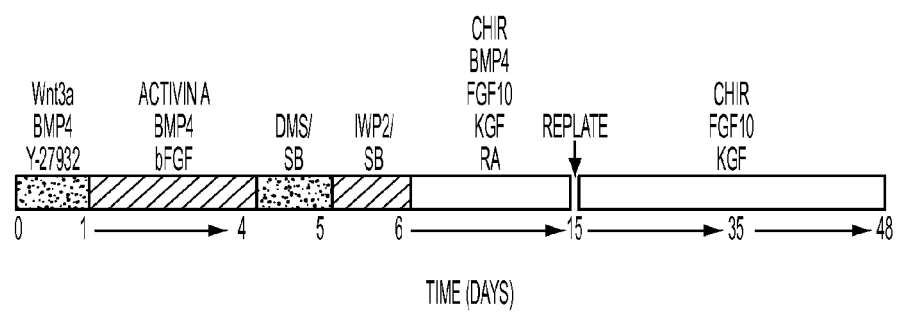
FIG. 14. Representative examples of the expression of markers of mature lung and airway epithelial cells after culturing sviPS cells according to the protocol shown on top of the figure. Immunofluorescence images represent reproducible results from 4 independent experiments.
Figure 14:
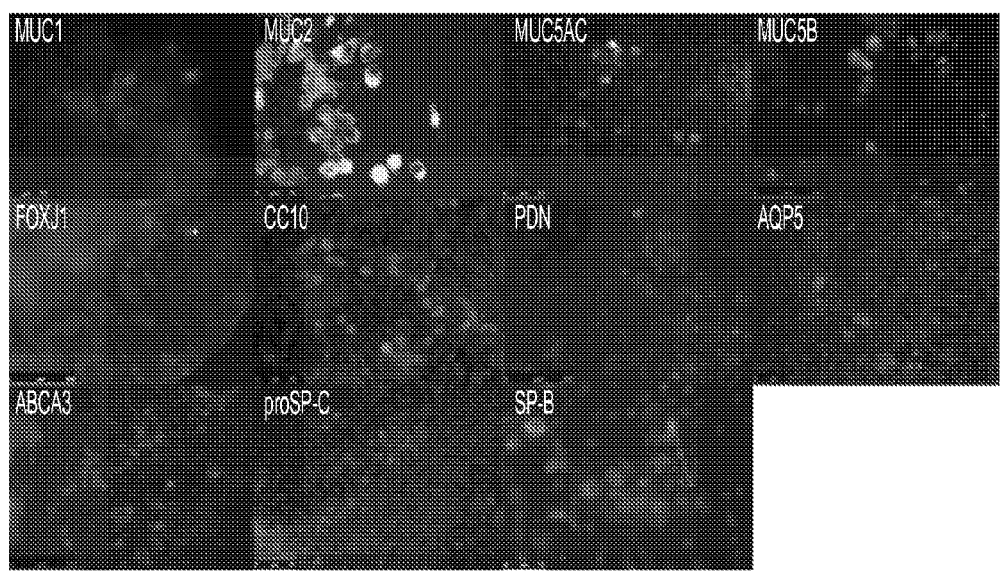
Figure 15:
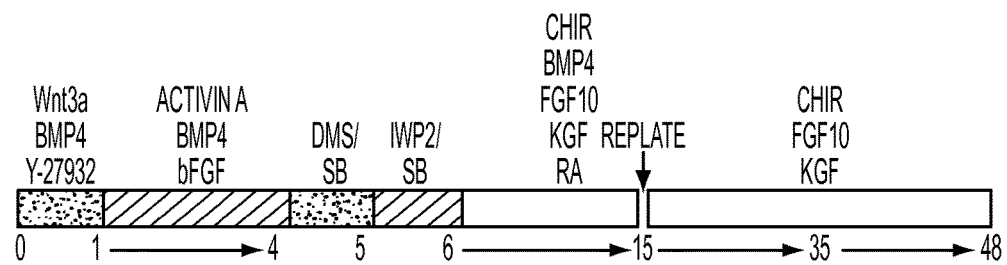
FIG. 15. Large magnification images of staining of cultures of sviPS cells (top) and RUES2 cells (bottom) cultured according to the protocol on top of the figure for MUC5B, MUC2 and CC-10. RUES2 cells were also stained for EPCAM to determine cell boundaries. Bright field is shown for sviPS cells.
Figure 15:
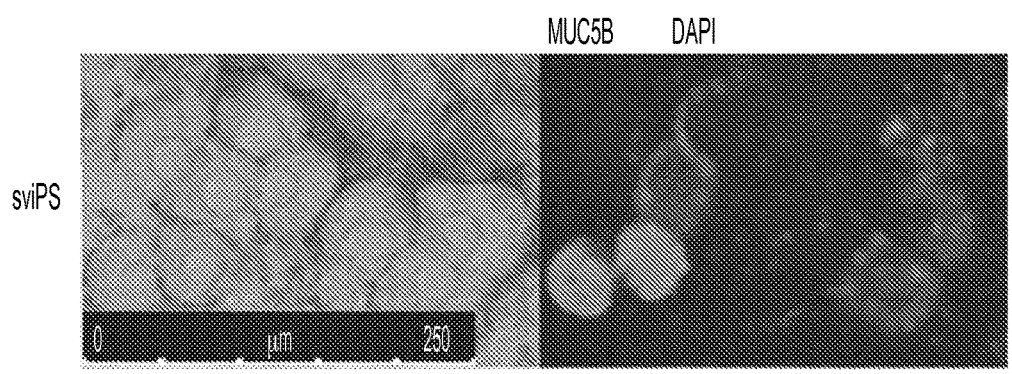
Figure 15:
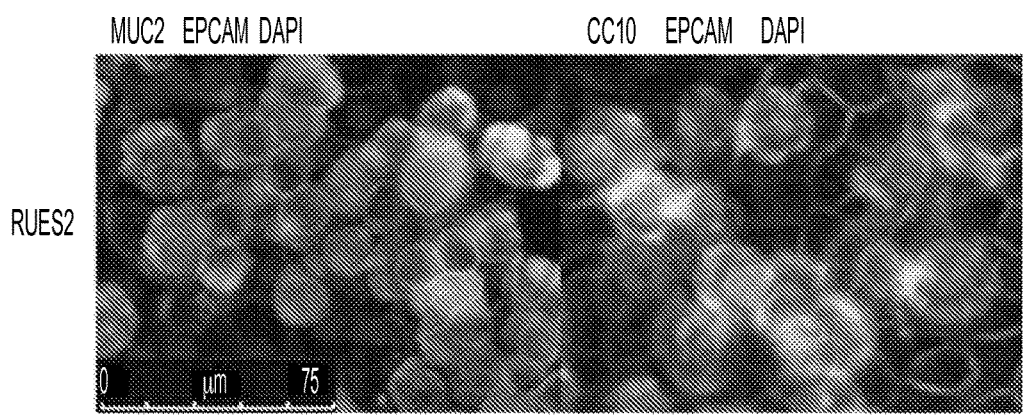

At d48, mucins (MUC1, MUC5AC, MUC2, MUC5B; goblet cells), FOXJ1 (ciliated cells), CC-10 (Clara cells), pro-SP-C and SP-B (ATII cells) as well as AQ5 and PDN (ATI cells) were observed (FIG. 5, FIGS. 13,14). Of the multiple mucins examined in our cultures, MUC1 is membrane-bound, while the other mucins are secreted. Consistent with this notion, staining for MUC5AC (not shown), MUC2 (FIG. 15) and MUC5B (FIG. 15) was observed, but not for MUC1 (not shown), outside cell boundaries as defined by EPCAM expression, and in structures that were discernible in bright field (FIG. 15). In addition, CC10, a protein secreted by Clara cells, was also detected outside of cell boundaries (FIG. 15). These findings suggest secretory activity of both goblet and Clara cells.

The cells positive for PDN and AQP5 displayed flat, crescent-shape nuclei at the periphery of the cells (FIG. 5 insets), a morphology typical of alveolar type I (ATI) cells. In many cells, SP-B expression occurred in a punctate pattern, suggestive of lamellar bodies of ATII cells where surfactant accumulates (FIG. 5, inset). At these later time points, expression of NKX2.1, which was >90% at day 25, became more variegated (FIG. 5, lower right panel). This was expected as NKX2.1 expression becomes restricted to Clara and ATII cells in human late fetal and postnatal lung[44, 45]. Nevertheless, SP-B+NKX2.1$^{dim}$ cells were detected as well (FIG. 5, lower right panel).

Figure 16:
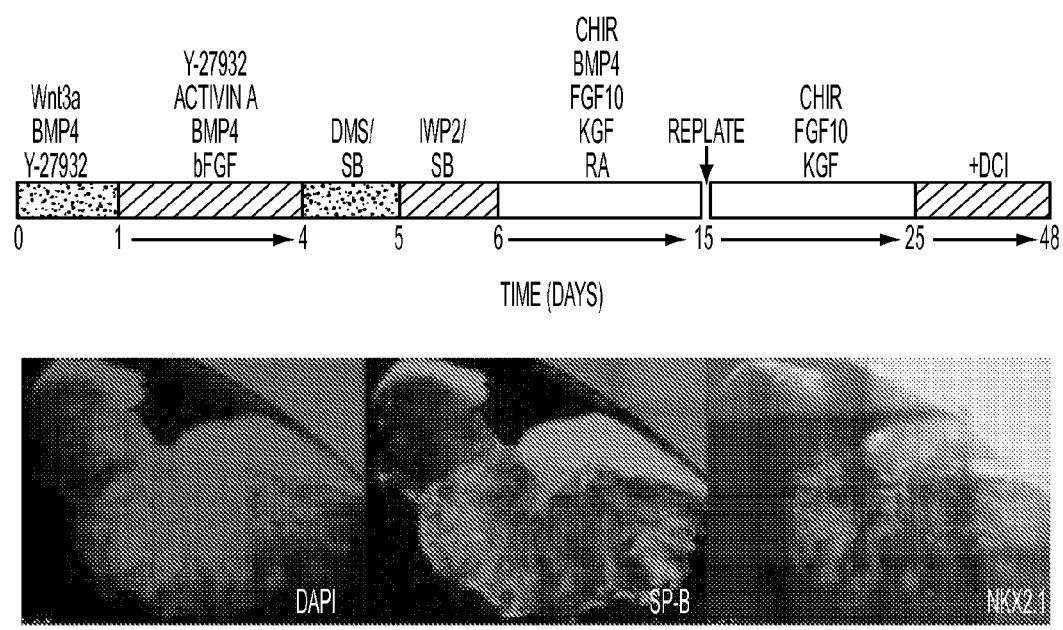
FIG. 16. Representative 10× whole culture tile scans of RUES2 cells cultured according to the protocol shown on top of the figure in the presence of DCI.
Figure 17:
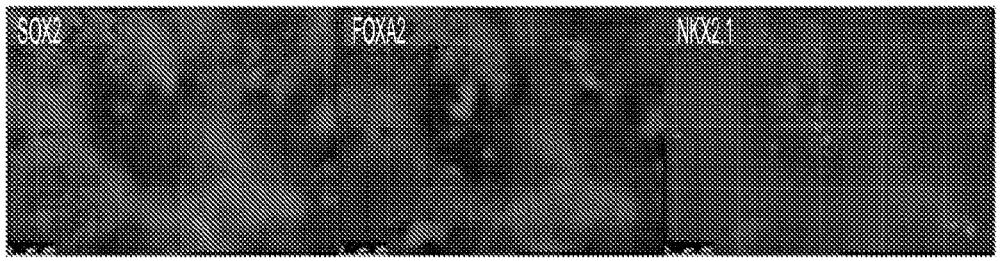
FIG. 17. Lung progenitor generation from hPSCs using the protocol published by Wong et al (ref. 9). Lower panels show lung field generation using our anteriorization protocol and the lung field induction protocol of Wong et al., as well as the anteriorization protocol of Wong et al. and our lung field induction protocol.
Figure 17:
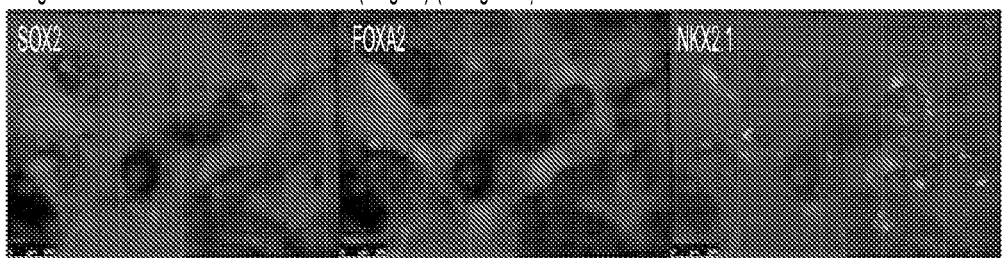
Figure 17:
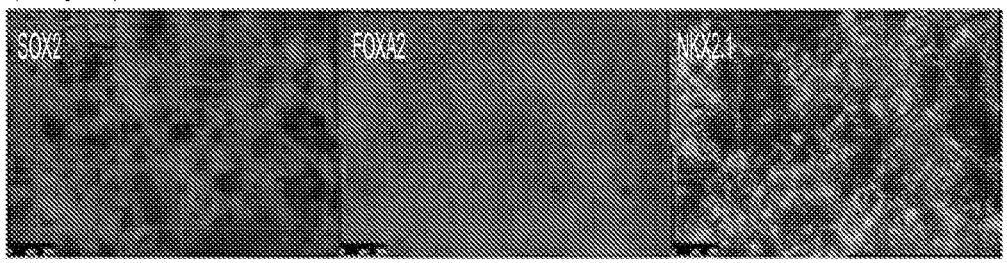

To further show that the cultures contained maturing ATII cells, the effect of adding dexamethasone, 8-bromo-cAMP and isobutylmethylxanthine (DCI) (FIG. 6a) was examined. DCI induces alveolar maturation in fetal mouse lung explants, and enhance surfactant protein expression in mES-derived lung progenitors[7, 47]. In the presence of DCI, SP-B+ cells became the predominant cell type (FIG. 6b, FIG. 16). Expression of mature SP-C was detected, although a much lower frequency than SP-B, suggesting incomplete maturation of ATII cells (FIG. 6b).

A unique, distinguishing functional characteristic of ATII cells is their uptake and recycling of surfactant proteins[48]. Therefore, BODIPY-labeled recombinant SP-B was added to the cultures. A large fraction of the cells showed uptake of the probe, in particular when cultured in the presence of DCI, while no uptake was observed in lung progenitors at d15 of culture (FIG. 6c). These data indicate that the ATII cells generated in our cultures are functional.

Figure 6D:
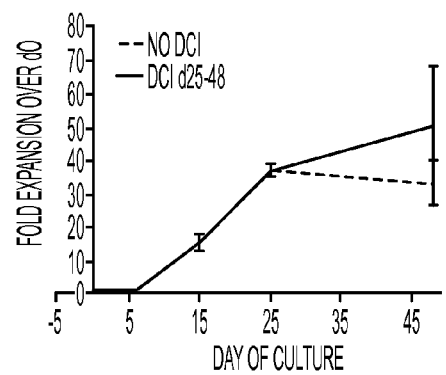

Cell number increased 35-fold up to d25, and did not increase appreciably after that (FIG. 6d). These data show that significant expansion of cell numbers occurred in the cultures, and suggest that the cessation of cellular expansion coincided with the beginning expression of lineage specific epithelial markers.

Example 6

Figure 18:
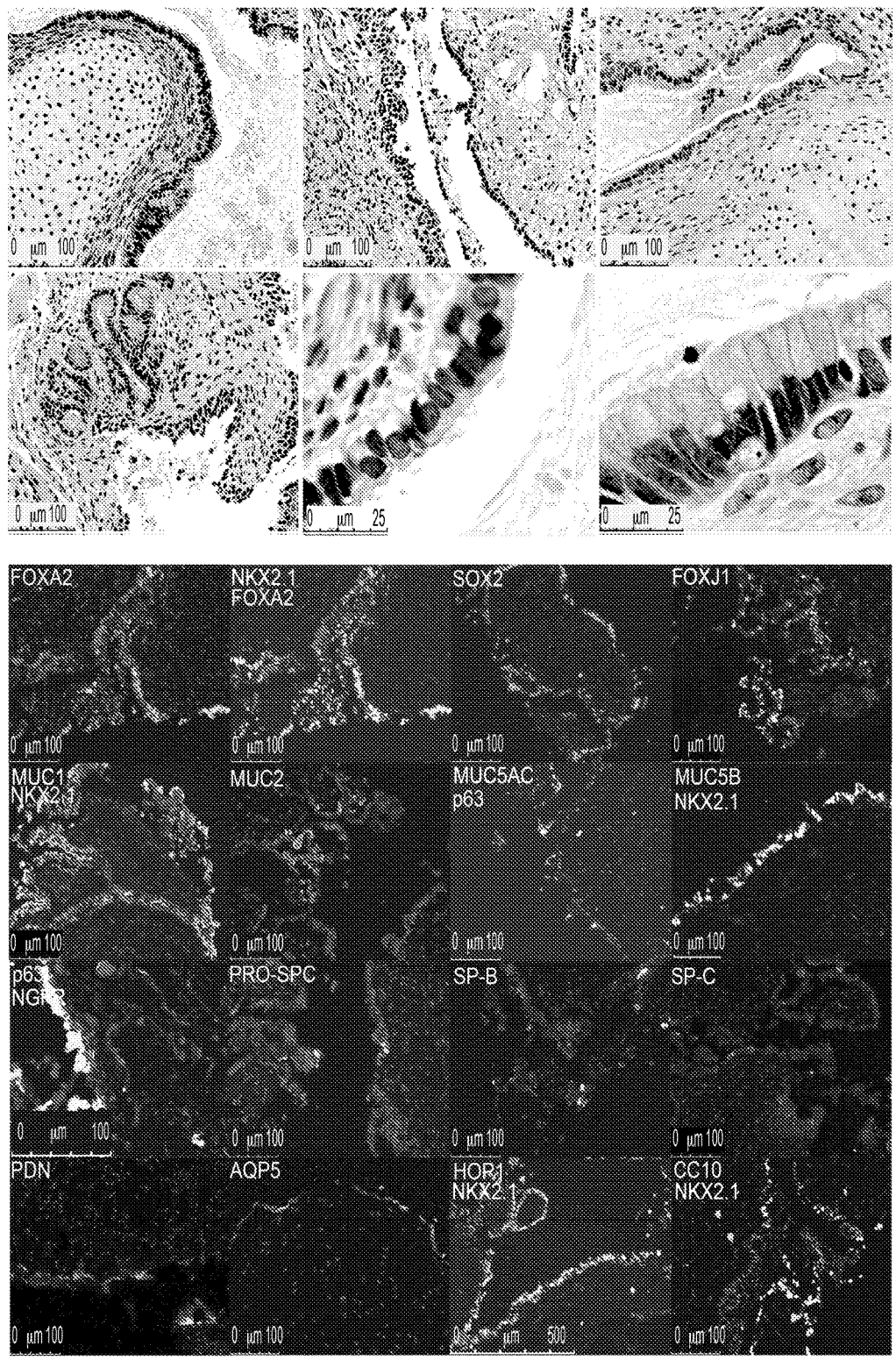
FIG. 18.(a) H/E staining of a growth arising 5 month after transplantation of d15 lung progenitor cells derived from RUES2 cells under the kidney capsule of immunocompromised mice. (b) Immunofluorescence analysis of the tissue from (a) stained for FOXA2, Nkx2.1, Sox2, p63, NGFR, MUC1, MUC2, MUC5AC, MUC5B, Foxj1, SP-B, pro-SP-C, SP-C, PDN, AQP5, HOP, and CC-10.
Figure 19:
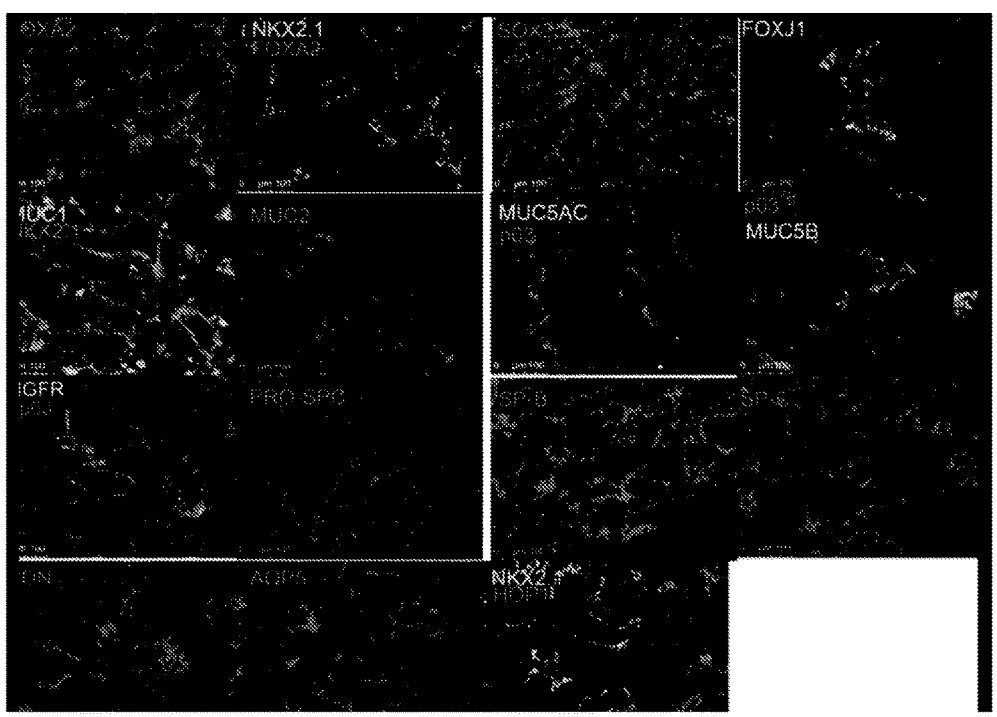
FIG. 19. Immunofluorescence analysis of human fetal lung tissue stained for FOXA2, Nkx2.1, Sox2, p63, NGFR, MUC1, MUC2, MUC5AC, MUC5B, Foxj1, SP-B, pro-SP-C, SP-C, PDN, AQP5, HOP, and CC-10.

In Vivo Differentiation of NKX2.1+FOXA2+ Cells into Cells Expressing Markers of Lung and Airway Epithelial Lineages To examine the differentiation potential in vivo, $10^6$ d15 cells lung and airway progenitors were transplanted under the kidney capsule of immunodeficient NSG mice. After 5 months, multiple macroscopic growths were observed, which contained cystic and tubular structures filled with acellular substance and lined by an epithelial layer that was varied from pseudostratified to a single layer of cells with either the appearance of ciliated or goblet cells, or consisting of flatter cells (FIG. 18a), and was uniformly FOXA2+ SOX2+NKX21+(FIG. 18b). Furthermore, glandular structures resembling submucosal glands were observed as well. All tested markers of mature lung and airway epithelial cells were detected. These included mucins (MUC1, MUC5AC, MUC2,;goblet cells), FOXJ1 (ciliated cells), p63 (basal cells), pro-SP-C, SP-C and SP-B (ATII cells) as well as AQ5, HOP1 and PDN (ATI cells) (FIG. 18b). These staining patterns were remarkably similar to those observed in human fetal lung (FIG. 19). In particular, while in adult lung, ATI cells do not express NKX2.1, we observed NKX2.1 expression in cells expressing the ATI marker HOP1, similar to fetal lung (FIG. 19). The numerous p63+ cells co-expressed NKX2.1 and NGFR, consistent with airway basal cells. The structures were surrounded by smooth muscle and cartilage, in addition to areas containing adipocytes (FIG. 18a). All cells, including the mesodermal cells were of human origin, as determined by staining with antibodies specific for human lamin (FIG. 18b). Together, these data indicate that d15 cells in our protocol almost exclusively give rise to lung and airway epithelial cells, in addition to mesodermal cells that adopted cell fates consistent with the mesodermal elements surrounding trachea and large airway. The data suggest that the pulmonary endoderm plays an instructive role on the development of the appropriate mesodermal element, likely originating from minimal amounts of contaminating mesoderm.

Discussion

These experiments are the first to show full differentiation of hESCs into a wide array of lung and airway cells with high efficiency in terms of purity and cellular expansion. >90% of the cells expressed NKX2.1, FOXA2 and SOX2, showing that these cultures consist of cells committed to a lung and airway. The efficiency of this protocol was variable in the iPS lines that were used, which is a reflection of the known variability in the lineage-specific differentiation potential of ES[29] and iPS[31, 32] lines. Among the set of ES lines tested in our studies (RUES1, RUES2, H1, H9, HES2), HES2 and RUES2 stood out in terms of AFE induction (not shown). The studies focused our studies on RUES2, as this is an NIH-approved line. Morphogen concentration and timing of addition or removal of factors should be optimized for each individual line, a notion suggested by the different optimal DE induction time in RUES2 vs. sviPS cells. It has also been recently shown that ES lines are heterogeneous with respect to Wnt signaling[30].

Provided is a new in vivo assay to test the function of lung and airway epithelial cells. The cells at various stages of differentiation in embodiments of the methods correspond to functional cells in vivo and it was validated by inhibiting or removing agonists to three signaling pathways that have been shown to be important for lung specification from the AFE in the mouse, RA, Wnt and BMP. Furthermore, actively secreting goblet and Clara cells as well as ATII-like cells capable of surfactant protein uptake were generated.

The data indicate that Wnt, BMP4 and RA are important for efficient induction of lung progenitors. These data suggest that a complex and hierarchical relation exists between TGF-β, BMP, Wnt, SHH and FGF2 signaling in the specification of AFE from DE.

The embodiments of the present invention represent a robust in vitro model system, where cell numbers are not limiting, that will complement mouse genetic approaches to study developmental lineage specification and maturation in the respiratory system. This is important for our understanding of lung development in humans, for disease modeling and drug screening, but also addresses one of the challenges to using autologous, iPSC-derived cells for seeding of decellularized lung matrices, which include generating sufficient numbers of cells with the appropriate variety and ratio of epithelial cells normally found in the lung.

Example 7

Ventralization and Formation of Spheres

DE was cultured in a TGF-beta inhibitor and a BMP inhibitor for at least 1 day, and then cultured in a Wnt signaling inhibitor for at least one day, as is described above. The adherent and non-adherent clusters of cells from these cultures were removed and replated/cultured in non-adherent culture conditions in full ventralization media [SFD supplemented with CHIR99021 (3 μM, WNT signaling agonist, Stemgent), human FGF10 (10 ng/mL, R&D Systems), human FGF7 (10 ng/mL, KGF, R&D Systems), human BMP4 (10 ng/mL, R&D Systems), and all-trans retinoic acid (50 nM, RA, Sigma)] until hollow spheres were formed. The hollow spheres started to appear around day 20-day25. About 15 days after the hollow spheres formed (day 40), obvious polyp-like ingrowths of cells into the spheres were observed. The hollow spheres could be further maintained to up to about d50 at which time the hollow spheres collapsed or ruptured and reformed well organized and/or polarized solid clumps. These collapsed spheres could be maintained for months.

REFERENCES

1. Green, M. D., Huang, S. X. & Snoeck, H. W. Stem cells of the respiratory system: From identification to differentiation into functional epithelium. *BioEssays: news and reviews in molecular, cellular and developmental biology* (2012).
2. Rock, J. R. & Hogan, B. L. Epithelial progenitor cells in lung development, maintenance, repair, and disease. *Annu Rev Cell Dev Biol* 27, 493-512 (2011).
3. Morrisey, E. E. & Hogan, B. L. Preparing for the first breath: genetic and cellular mechanisms in lung development. *Dev Cell* 18, 8-23 (2010).
4. Rawlins, E. L., Clark, C. P., Xue, Y. & Hogan, B. L. The Id2+ distal tip lung epithelium contains individual multipotent embryonic progenitor cells. *Development* 136, 3741-3745 (2009).
5. Green, M. D. et al. Generation of anterior foregut endoderm from human embryonic and induced pluripotent stem cells. *Nature biotechnology* 29, 267-272 (2011).
6. Mou, H. et al. Generation of Multipotent Lung and Airway Progenitors from Mouse ESCs and Patient-Specific Cystic Fibrosis iPSCs. *Cell Stem Cell* 10, 385-397 (2012).
7. Longmire, T. A. et al. Efficient derivation of purified lung and thyroid progenitors from embryonic stem cells. *Cell Stem Cell* 10, 398-411 (2012).
8. Wong, A. P. et al. Directed differentiation of human pluripotent stem cells into mature airway epithelia expressing functional CFTRTR protein. *Nature biotechnology* 30, 876-882 (2012).

9. Kubo, A. et al. Development of definitive endoderm from embryonic stem cells in culture. *Development* 131, 1651-1662 (2004).
10. Nostro, M. C. & Keller, G. Generation of beta cells from human pluripotent stem cells: Potential for regenerative medicine. *Seminars in cell & developmental biology* (2012).
11. Nostro, M. C. et al. Stage-specific signaling through TGFbeta family members and WNT regulates patterning and pancreatic specification of human pluripotent stem cells. *Development* 138, 861-871 (2011).
12. D'Amour, K. A. et al. Efficient differentiation of human embryonic stem cells to definitive endoderm. *Nature biotechnology* 23, 1534-1541 (2005).
13. Gouon-Evans, V. et al. BMP-4 is required for hepatic specification of mouse embryonic stem cell-derived definitive endoderm. *Nature biotechnology* 24, 1402-1411 (2006).
14. Goss, A. M. et al. Wnt2/2b and beta-catenin signaling are necessary and sufficient to specify lung progenitors in the foregut. *Dev Cell* 17, 290-298 (2009).
15. Bellusci, S., Grindley, J., Emoto, H., Itoh, N. & Hogan, B. L. Fibroblast growth factor 10 (FGF10) and branching morphogenesis in the embryonic mouse lung. *Development* 124, 4867-4878 (1997).
16. Bellusci, S., Henderson, R., Winnier, G., Oikawa, T. & Hogan, B. L. Evidence from normal expression and targeted misexpression that bone morphogenetic protein (Bmp-4) plays a role in mouse embryonic lung morphogenesis. *Development* 122, 1693-1702 (1996).
17. Domyan, E. T. et al. Signaling through BMP receptors promotes respiratory identity in the foregut via repression of Sox2. *Development* 138, 971-981 (2011).
18. Li, Y., Gordon, J., Manley, N. R., Litingtung, Y. & Chiang, C. Bmp4 is required for tracheal formation: a novel mouse model for tracheal agenesis. *Developmental biology* 322, 145-155 (2008).
19. Chen, F. et al. A retinoic acid-dependent network in the foregut controls formation of the mouse lung primordium. *J Clin Invest* 120, 2040-2048 (2010).
20. Yamamoto, M. et al. Nodal antagonists regulate formation of the anteroposterior axis of the mouse embryo. *Nature* 428, 387-392 (2004).
21. Perea-Gomez, A. et al. Nodal antagonists in the anterior visceral endoderm prevent the formation of multiple primitive streaks. *Dev Cell* 3, 745-756 (2002).
22. del Barco Barrantes, I., Davidson, G., Grone, H. J., Westphal, H. & Niehrs, C. Dkk1 and noggin cooperate in mammalian head induction. *Genes Dev* 17, 2239-2244 (2003).
23. Yu, P. B. et al. Dorsomorphin inhibits BMP signals required for embryogenesis and iron metabolism. *Nature chemical biology* 4, 33-41 (2008).
24. Inman, G. J. et al. SB-431542 is a potent and specific inhibitor of transforming growth factor-beta superfamily type I activin receptor-like kinase (ALK) receptors ALK4, ALK5, and ALK7. *Molecular pharmacology* 62, 65-74 (2002).
25. Chen, B. et al. Small molecule-mediated disruption of Wnt-dependent signaling in tissue regeneration and cancer. *Nature chemical biology* 5, 100-107 (2009).
26. Bennett, C. N. et al. Regulation of Wnt signaling during adipogenesis. *The Journal of biological chemistry* 277, 30998-31004 (2002).
27. Fusaki, N., Ban, H., Nishiyama, A., Saeki, K. & Hasegawa, M. Efficient induction of transgene-free human pluripotent stem cells using a vector based on Sendai virus, an RNA virus that does not integrate into the host genome. *Proceedings of the Japan Academy. Series B, Physical and biological sciences* 85, 348-362 (2009).
28. Warren, L. et al. Highly efficient reprogramming to pluripotency and directed differentiation of human cells with synthetic modified mRNA. *Cell Stem Cell* 7, 618-630 (2010).
29. Osafune, K. et al. Marked differences in differentiation propensity among human embryonic stem cell lines. *Nature biotechnology* 26, 313-315 (2008).
30. Blauwkamp, T. A., Nigam, S., Ardehali, R., Weissman, I. L. & Nusse, R. Endogenous Wnt signalling in human embryonic stem cells generates an equilibrium of distinct lineage-specified progenitors. *Nature communications* 3, 1070 (2012).
31. Bock, C. et al. Reference Maps of human ES and iPS cell variation enable high-throughput characterization of pluripotent cell lines. *Cell* 144, 439-452 (2011).
32. Boulting, G. L. et al. A functionally characterized test set of human induced pluripotent stem cells. *Nature biotechnology* 29, 279-286 (2011).
33. Kimura, S. et al. The T/ebp null mouse: thyroid-specific enhancer-binding protein is essential for the organogenesis of the thyroid, lung, ventral forebrain, and pituitary. *Genes Dev* 10, 60-69 (1996).
34. Kriks, S. et al. Dopamine neurons derived from human ES cells efficiently engraft in animal models of Parkinson's disease. *Nature* 480, 547-551 (2011).
35. van den Brink, G. R. Hedgehog signaling in development and homeostasis of the gastrointestinal tract. *Physiol Rev* 87, 1343-1375 (2007).
36. Harris-Johnson, K. S., Domyan, E. T., Vezina, C. M. & Sun, X. beta-Catenin promotes respiratory progenitor identity in mouse foregut. *Proc Natl Acad Sci USA* 106, 16287-16292 (2009).
37. Que, J., Choi, M., Ziel, J. W., Klingensmith, J. & Hogan, B. L. Morphogenesis of the trachea and esophagus: current players and new roles for noggin and Bmps. *Differentiation; research in biological diversity* 74, 422-437 (2006).
38. Weaver, M., Yingling, J. M., Dunn, N. R., Bellusci, S. & Hogan, B. L. Bmp signaling regulates proximal-distal differentiation of endoderm in mouse lung development. *Development* 126, 4005-4015 (1999).
39. Shu, W. et al. Wnt/beta-catenin signaling acts upstream of N-myc, BMP4, and FGF signaling to regulate proximal-distal patterning in the lung. *Developmental biology* 283, 226-239 (2005).
40. Post, M. et al. Keratinocyte growth factor and its receptor are involved in regulating early lung branching. *Development* 122, 3107-3115 (1996).
41. Malpel, S., Mendelsohn, C. & Cardoso, W. V. Regulation of retinoic acid signaling during lung morphogenesis. *Development* 127, 3057-3067 (2000).
42. Wongtrakool, C. et al. Down-regulation of retinoic acid receptor alpha signaling is required for sacculation and type I cell formation in the developing lung. *The Journal of biological chemistry* 278, 46911-46918 (2003).
43. Rock, J. R. et al. Basal cells as stem cells of the mouse trachea and human airway epithelium. *Proc Natl Acad Sci USA* 106, 12771-12775 (2009).
44. Hosgor, M., Ijzendoorn, Y., Mooi, W. J., Tibboel, D. & De Krijger, R. R. Thyroid transcription factor-1 expression during normal human lung development and in patients with congenital diaphragmatic hernia. *Journal of pediatric surgery* 37, 1258-1262 (2002).

45. Stahlman, M. T., Gray, M. E. & Whitsett, J. A. Expression of thyroid transcription factor-1(TTF-1) in fetal and neonatal human lung. *The journal of histochemistry and cytochemistry: official journal of the Histochemistry Society* 44, 673-678 (1996).
46. Khoor, A., Stahlman, M. T., Gray, M. E. & Whitsett, J. A. Temporal-spatial distribution of SP-B and SP-C proteins and mRNAs in developing respiratory epithelium of human lung. *The journal of histochemistry and cytochemistry: official journal of the Histochemistry Society* 42, 1187-1199 (1994).
47. Gonzales, L. W., Guttentag, S. H., Wade, K. C., Postle, A. D. & Ballard, P. L. Differentiation of human pulmonary type II cells in vitro by glucocorticoid plus cAMP. *American journal of physiology. Lung cellular and molecular physiology* 283, L940-951 (2002).
48. Whitsett, J. A., Wert, S. E. & Weaver, T. E. Alveolar surfactant homeostasis and the pathogenesis of pulmonary disease. *Annual review of medicine* 61, 105-119 (2010).

What is claimed is:

1. A method comprising culturing-Anterior Foregut Epithelial-(AFE) cells in a Wnt signaling agonist, retinoic acid (RA) at a concentration of from 10 nanomoles to 100 nanomoles, 10 to 50 nanomoles, or 50 to 100 nanomoles and an agent that activates BMP4 signaling or BMP4 for at least 9 days, thereby producing lung and airway progenitor cells that express both NKX2.1 and FOXA2.

2. The method of claim 1, wherein the Wnt signaling agonist is a member selected from the group comprising a glycogen synthase kinase (GSK) inhibitor, a recombinant canonical Wnt agonist, norrin, r-spondin, $C_{19}H_{18}N_4O_3$, and (2-amino-4-[3,4-(methylenedioxy)benzylamino]-6-(3-methoxyphenyl)pyrimidine.

3. The method of claim 1, wherein the AFE cells are made by
(a) culturing mammalian definitive endoderm cells in a transforming growth factor (TGF)-beta inhibitor and a bone morphogenic protein (BMP) inhibitor for at least 1 day, and
(b) then culturing the cells of step (a) in a Wnt signaling inhibitor and a TGF-beta inhibitor for at least one day.

4. The method of claim 3, wherein in step (a) the inhibitor of BMP is a member selected from the group comprising noggin, dorsomorphin (DSM), LDN 193189, sclerostin, chordin, growth differentiation factor 3 (GDF3) protein, connective tissue growth factor (CTGF), 4-[6-[4-(1-methylethoxy)phenyl]pyrazolo[1,5-a]pyrimidin-3-yl]-quinoline (DMH1), inhibin, BMP-3, follistatin, and gremlin.

5. The method of claim 3, wherein said definitive endoderm cell is an embryoid body.

6. The method of claim 3, wherein the TGF-beta inhibitor is a member selected from the group comprising LY 364947, SB 431542, A 83-01, SD 208, GW 788388, SB 505124, SB 525334, RepSox, casein kinase 1 inhibitor, D4476, 4-(2-aminoethyl)benzenesulfonyl fluoride hydrochloride (AEBSF) hydrochloride, and LY 2157299, and the BMP inhibitor is a member selected from the group comprising noggin, dorsomorphin (DSM), LDN193189, sclerostin, chordin, growth differentiation factor 3 (GDF3) protein, CTGF, DMH1, inhibin, BMP-3, follistatin, and gremlin.

7. The method of claim 3, where the Wnt signaling inhibitor of step (b) is a member selected from the group comprising IWP2, Dickkopf (Dkk), RNAi targeting beta-catenin, RNAi targeting low density lipoprotein receptor-related protein (LRP), RNAi targeting dishevelled, dominant negative dishevelled, dominant negative T-cell-specific transcription factor (TCF), Axin, Wnt inhibitory factor 1 (WIF-1), secreted Frizzled-related proteins (SFRP), Cerberus, Frzb, Wise, Sclerostin (SOST), Wnt inhibitory factor (WIF), insulin-like growth factor-binding protein (IGFBP), Shisa, Waif1, Adenomatosis polyposis coli downregulated 1 (APCDD1), and Tiki1.

8. The method of claim 1 further comprising
(a) selecting clumps of the lung progenitor cells, and
(b) then culturing the clumps of lung progenitor cells in a Wnt signaling agonist and fibroblast growth factor (FGF) agonist for a duration of time until airway and lung epithelial cells are detected.

9. The method of claim 8, further comprising adding keratinocyte growth factor (KGF), and wherein the FGF comprises FGF10 and/or FGF7, and or both.

10. The method of claim 8, wherein the airway and lung epithelial cells comprise goblet cells, clara cells, ciliated cells, type I alveolar cells, basal cells and type II alveolar epithelial cells or combinations thereof.

11. The method of claim 8, further comprising adding dexamethasone, 8-bromo-cAMP and isobutylmethylxanthine (DCI) to increase the production and maturation of alveolar type II cells after culturing the clumps in a Wnt signaling agonist and FGF agonist for at least about 6 days.

12. The method of claim 8, wherein the airway and lung epithelial cells express NKX2.1, Forkhead box (FOXA2) and SOX2.

13. The method of claim 1, wherein the AFE cells are human.

14. The method of claim 1, wherein the AFE cells are provided by a subject in need of an autologous lung or airway progenitor cell transplant, or an autologous lung or airway epithelial cell transplant or from a subject having a lung or airway disease.

15. The method of claim 2, wherein the Wnt agonist is either Wnt3a or CHIR99021.

* * * * *